(12) United States Patent
Mwikirize et al.

(10) Patent No.: US 11,426,142 B2
(45) Date of Patent: Aug. 30, 2022

(54) COMPUTER VISION SYSTEMS AND METHODS FOR REAL-TIME LOCALIZATION OF NEEDLES IN ULTRASOUND IMAGES

(71) Applicant: Rutgers, The State University of New Jersey, New Brunswick, NJ (US)

(72) Inventors: Cosmas Mwikirize, Wakiso (UG); John L. Nosher, Basking Ridge, NJ (US); Ilker Hacihaliloglu, Jersey City, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 17/268,321

(22) PCT Filed: Aug. 13, 2019

(86) PCT No.: PCT/US2019/046364
§ 371 (c)(1),
(2) Date: Feb. 12, 2021

(87) PCT Pub. No.: WO2020/036968
PCT Pub. Date: Feb. 20, 2020

(65) Prior Publication Data
US 2021/0330289 A1 Oct. 28, 2021

Related U.S. Application Data

(60) Provisional application No. 62/718,090, filed on Aug. 13, 2018.

(51) Int. Cl.
*A61B 8/00* (2006.01)
*G06T 7/194* (2017.01)
(Continued)

(52) U.S. Cl.
CPC ............. *A61B 8/4245* (2013.01); *G06N 3/04* (2013.01); *G06T 7/194* (2017.01); *G06T 7/70* (2017.01); *G06T 2207/10132* (2013.01)

(58) Field of Classification Search
CPC . G06T 2207/10132; G06T 7/70; G06T 7/194; G06N 3/04; A61B 8/4245
See application file for complete search history.

(56) References Cited

U.S. PATENT DOCUMENTS 8,357,094 B2 * 1/2013 Mo ....................... G01S 7/5206
600/438
9,226,729 B2 * 1/2016 Tashiro ................ A61B 8/5223
(Continued)

FOREIGN PATENT DOCUMENTS

| CN | 103886617 A | 6/2014 |
|---|---|---|
| CN | 104248454 B | 6/2016 |
| EP | 2735271 A1 | 5/2014 |

OTHER PUBLICATIONS

Mwikirize et al. "Single Shot Needle Tip Localization in 2D Ultrasound" Springer Nature Switzerland AG 2019, MICCAI 2019, LNCS 11768, pp. 637-645.*
(Continued)

*Primary Examiner* — Mia M Thomas
(74) *Attorney, Agent, or Firm* — McCarter & English, LLP

(57) ABSTRACT

Computer vision systems and methods for real-time localization of a needle in an ultrasound video are provided. The method includes a step of receiving at a processor a plurality of frames from the ultrasound video. The method also includes the step of identifying by the processor one of the plurality of frames as a background image and a frame adjacent to the background image as a current image. The method further includes the step of performing by the processor a bitwise complement operation on the back-
(Continued)

ground image to generate a complement image. Moreover, the method includes the step of performing by the processor a pointwise logical AND operation on the complement image and the current image to identify the location of the needle.

29 Claims, 15 Drawing Sheets

(51) Int. Cl.
*G06T 7/70* (2017.01)
*G06N 3/04* (2006.01)

(56) References Cited

U.S. PATENT DOCUMENTS

| | | | |
|---|---|---|---|
| 9,364,294 B2* | 6/2016 | Razzaque | A61B 34/25 |
| 9,398,936 B2* | 7/2016 | Razzaque | A61B 34/10 |
| 9,561,019 B2* | 2/2017 | Mihailescu | A61B 6/4417 |
| 9,792,686 B2* | 10/2017 | Zalev | A61B 5/7225 |
| 9,858,496 B2 | 1/2018 | Sun et al. | |
| 9,881,234 B2 | 1/2018 | Huang et al. | |
| 10,206,655 B2* | 2/2019 | Woo | A61B 6/105 |
| 10,213,110 B2* | 2/2019 | Wang | A61B 5/0084 |
| 10,232,194 B2* | 3/2019 | Schlosser | A61B 6/5247 |
| 2003/0189980 A1 | 10/2003 | Dvir et al. | |
| 2004/0049109 A1* | 3/2004 | Thornton | A61B 8/12 |
| | | | 600/427 |
| 2006/0171594 A1 | 8/2006 | Avidan et al. | |
| 2007/0167801 A1 | 7/2007 | Webler et al. | |
| 2008/0146932 A1 | 6/2008 | Chalana et al. | |
| 2012/0046971 A1 | 2/2012 | Walker et al. | |
| 2013/0077442 A1 | 3/2013 | Hersey | |
| 2014/0140597 A1* | 5/2014 | Barzelay | A61B 6/52 |
| | | | 382/130 |
| 2015/0209599 A1* | 7/2015 | Schlosser | A61B 6/4417 |
| | | | 600/427 |
| 2015/0256761 A1* | 9/2015 | Umezawa | A61B 8/14 |
| | | | 348/77 |
| 2015/0320374 A1* | 11/2015 | Uehara | A61B 8/06 |
| | | | 600/424 |
| 2015/0346303 A1 | 12/2015 | Hu et al. | |
| 2016/0048737 A1* | 2/2016 | Kam | A61B 8/4245 |
| | | | 382/131 |
| 2016/0155227 A1* | 6/2016 | Chae | A61B 8/469 |
| | | | 382/131 |
| 2016/0242811 A1 | 8/2016 | Sadiq et al. | |
| 2016/0317118 A1 | 11/2016 | Parthasarathy et al. | |
| 2017/0027701 A1* | 2/2017 | Mahfouz | A61F 2/4003 |
| 2017/0143312 A1* | 5/2017 | Hedlund | A61B 6/037 |
| 2017/0188990 A1* | 7/2017 | Von Allmen | A61B 8/0841 |
| 2017/0206431 A1 | 7/2017 | Sun et al. | |
| 2017/0258451 A1* | 9/2017 | Sakanashi | A61B 8/5223 |
| 2018/0075628 A1 | 3/2018 | Teare | |
| 2018/0158209 A1* | 6/2018 | Fine | G06K 9/66 |
| 2018/0173971 A1 | 6/2018 | Jia et al. | |
| 2018/0325602 A1* | 11/2018 | Bharat | A61B 34/10 |
| 2018/0333112 A1* | 11/2018 | Weber | A61B 6/5211 |
| 2018/0338793 A1* | 11/2018 | Sulkin | A61B 18/1492 |
| 2018/0368807 A1* | 12/2018 | Van De Pas | A61B 8/4444 |
| 2018/0368883 A1* | 12/2018 | Rossa | G06T 7/70 |
| 2019/0019037 A1 | 1/2019 | Kadav et al. | |
| 2019/0069882 A1* | 3/2019 | Moctezuma de la Barrera | |
| | | | A61B 34/10 |
| 2019/0231441 A1* | 8/2019 | Vaughan | A61B 34/20 |
| 2019/0247130 A1* | 8/2019 | State | A61B 18/1477 |
| 2019/0336107 A1* | 11/2019 | Hope Simpson | G01S 15/8979 |
| 2019/0336108 A1* | 11/2019 | Hope Simpson | A61B 8/0891 |
| 2019/0378293 A1* | 12/2019 | Mwikirize | G06T 5/20 |
| 2020/0037983 A1* | 2/2020 | Poland | G06T 7/20 |
| 2020/0076842 A1* | 3/2020 | Zhou | G06N 3/0454 |
| 2020/0311943 A1 | 10/2020 | Dai et al. | |
| 2020/0342305 A1 | 10/2020 | Du et al. | |
| 2021/0068791 A1* | 3/2021 | Gebre | A61B 8/5207 |
| 2021/0110532 A1 | 4/2021 | Braman et al. | |

OTHER PUBLICATIONS

Hacihaliloglu et al. "Projection Based Phase Features for Localization of a Needle Tip in 2D Curvilinear Ultrasound" Springer Nature Switzerland AG 2015, MICCAI 2015, LNCS 9349, pp. 347-354.*
Pourtaherian et al. "Improving Needle Detection in 3D Ultrasound Using Orthogonal-Plane Convolutional Networks" Springer International Publishing AG 2017, MICCAI 2017, Part II, LNCS 10434, pp. 610-618.*
International Search Report of the International Searching Authority dated Oct. 29, 2019, issued in connection with International Application No. PCT/US2019/046364 (3 pages).
Written Opinion of the International Searching Authority dated Oct. 29, 2019, issued in connection with International Application No. PCT/US2019/046364 (4 pages).
Mwikirize, et al., "Learning Needle Tip Localization from Digital Subtraction in 2D Ultrasound," International Journal of Computer Assisted Radiology and Surgery, Mar. 25, 2019 (10 pages).
Dong, et al., "A Novel Method for Enhanced Needle Localization Using Ultrasound-Guidance," ISVC 2009: Advances in Visual Computing, Nov. 30, 2009, pp. 914-923 (12 pages).
Renfrew, et al., "Active Localization and Tracking of Needle and Target in Robotic Image-Guided Intervention Systems, " Auton Robots: 42(1):83-97, Jun. 12, 2017 (39 pages).
Neubach, et al., "Ultrasound-Guided Robot for Flexibile Needle Steering," IEEE Transactions on Biomedical Engineering, vol. 57, No. 4, Apr. 4, 2010 (8 pages).
Mwikirize, et al., "Signal Attenuation Maps for Needle Enhancement and Localization in 2D Ultrasound," International Journal of Computer Assisted Radiology and Surgery, 13, pp. 363-374 (2018) (12 pages).
Klambauer, et al., "Self-Normalizing Neural Networks," arXiv:1706.02515v5, Sep. 7, 2017 (102 pages).
Mathiassen, et al., "Robust Real-Time Needle Tracking in 2-D Ultrasound Images Using Statistical Filtering," IEEE Transactions on Control Systems Technology, vol. 25, No. 3, pp. 966-978, May 2017 (13 pages).
Pourtaherian, et al., "Robust and Semantic Needle Detection in 3D Ultrasound Using Orthogonal-Plane Convolutional Neural Networks," International Journal of Computer Assisted Radiology and Surgery 13, pp. 1321-1333 (2018) (13 pages).
Priester, et al., "Robotic Ultrasound Systems in Medicine," IEEE Transactions on Ultrasonics, Ferroelectrics, and Frequency Control, vol. 60, No. 3, pp. 507-523, Mar. 2013 (17 pages).
Fevre, et al., "Reduced Variability and Execution Time to Reach a Target with a Needle GPS System: Comparison Between Physicians, Residents and Nurse Anaesthetists," Anaesth Crit Care Pain Med 37, pp. 55-60 (2018) (6 pages).
Prasad, et al., "Real-Time Ultrasound-Guided Percutaneous Renal Biopsy with Needle Guide by Nephrologists Decreases Post-Biopsy Complications," Clin Kidney J, 8: pp. 151-156 (2015) (6 pages).
Clendenen, et al., "Real-Time Three-Dimensional Ultrasound-Assisted Axillary Plexus Block Defines Soft Tissue Planes," International Anesthesia Research Society, vol. 108, No. 4, pp. 1347-1350, Apr. 2009 (4 pages).
Grady, "Random Walks for Image Segmentation," IEEE Transactions on Pattern Analysis and Machine Intelligence, vol. 28, No. 11, Nov. 2006 (16 pages).
Xia, et al., "Looking Beyond the Imaging Plane: 3D Needle Tracking with a Linear Array Ultrasound Probe," Scientific Reports 7:3674 (2017) (9 pages).
Xia, et al.," In-Plane Ultrasonic Needle Tracking Using a Fiber-Optic Hydrophone," Med Phys 42, pp. 5983-5991, Oct. 2015 (16 pages).
Welleweerd, et al., "Design of an End Effector for Robot-Assisted Ultrasound-Guided Breast Biopsies," International Journal of Computer Assisted Radiology and Surgery 15, pp. 681-690 (2020) (10 pages).

(56) References Cited

OTHER PUBLICATIONS

Redmon, et al., "You Only Look Once: Unified, Real-Time Object Detection," arXiv:1506.02640v5, May 9, 2016 (10 pages).
Neubach, et al., "Ultrasound-Guided Robot for Flexible Needle Steering," IEEE Transactions on Biomedical Engineering, vol. 57, No. 4, pp. 799-805, Apr. 2010 (7 pages).
Huang, et al., "The Principles and Procedures of Ultrasound-Guided Anesthesia Techniques," Cureus 10(7): e2980 (2018) (8 pages).
Najafi, et al., "Single-Camera Closed-Form Real-Time Needle Tracking for Ultrasound-Guided Needle Insertion," Ultrasound in Med. & Biol., vol. 41, No. 10, pp. 2663-2676 (2015) (14 pages).
Mwikirize, et al., "Single Shot Needle Localization in 2D Ultrasound," MICCAI 2019, LNCS 11768, pp. 637-645 (9 pages).
Marhofer, et al., "Safe performance of Peripheral Regional Anaesthesia: The Significance of Ultrasound Guidance," Anaesthesia 72, pp. 431-434 (2017) (4 pages).
Kim, et al., "Practical Guidelines for Ultrasound-Guided Core Needle Biopsy of Soft-Tissue Lesions: Transformation from Beginner to Specialist," Korean Journal of Radiology 18(2), pp. 361-369 (2017) (9 pages).
Umbarje, et al., "Out-of-Plane Brachial Plexus Block with a Novel SonixGPS (TM) Needle Tracking System," Anaesthesia 68: pp. 433-434 (2013) (2 pages).
Gadsden, et al., "Evaluation of the eZono 4000 with eZGuide for Ultrasound-Guided Procedures," Expert Review of Medical Devices 12(3), pp. 251-261 (2015) (12 pages).
McVicar, et al., "Novice Performance of Ultrasound-Guided Nedling Skills: Effect of a Needle Guidance System," Regional Anesthesia and Pain Medicine, vol. 40, No. 2, pp. 150-153, Mar.-Apr. 2015 (4 pages).
Mwikirize, et al., "Local Phase-Based Learning for Needle Detection and Localization in 3d Ultrasound," In Computer Assisted and Robotic Endoscopy and Clinical Image-Based Procedures, Sep. 14, 2017, Springer, Cham., pp. 108-115 (8 pages).
Mwikirize, et al., "Time-Aware Deep Neural Networks for Needle Tip Localization in 2D Ultrasound," International Journal of Computer Assisted Radiology and Surgery (2021) (9 pages).
Girshick, "Fast R-CNN," arXiv:1504.08083v2, Sep. 27, 2015 (9 pages).
Krizhevsky, et al., "Imagenet Classification with Deep Convolutional Neural Networks," Advances in Neural Information Processing Systems (2012) (9 pages).
Simonyan, et al., "Very Deep Convolutional Network for Large-Scale Image Recognition," arXiv:1409.1556v6, Apr. 10, 2015 (14 pages).
Zeiler, et al. "Visualizing and Understanding Convolutional Neural Networks," arXiv:1311.2901v3, Nov. 28, 2013 (11 pages).
Krizhevsky, "Learning Multiple Layers of Features from Tiny Images," CIFAR10 dataset, Apr. 8, 2009 (60 pages).
Huynh, et al., "Digital Mammographic Tumor Classification Using Transfer Learning from Deep Convolutional Neural Networks," Journal of Medical Imaging, vol. 3(3) (2016) (6 pages).
Ameri, et al., "Development of a High Frequency Single-Element Ultrasound Needle Transducer for Anesthesia Delivery," In: Proc. SPIE Medical Imaging: Ultrasonic Imaging and Tomography, vol. 10139 (2017) (8 pages).
Huang, et al., "Imaging Artifacts of Medical Instruments in Ultrasound-Guided Interventions," American Institute of Ultrasound in Medicine 2007, vol. 26, pp. 1303-1322 (20 pages).
Wang, et al., "Active Contour Model Coupling with Backward Diffusion for Medical Image Segmentation," 6th International Conference on Biomedical Engineering and Informatics (2013) (5 pages).
Mwikirize, et al., "Convolutional Neural Networks for Real-Time Needle Detection and Localization in 2D Ultrasound," International Journal of Computer Assisted Radiology and Surgery, Mar. 6, 2018 (11 pages).
Extended European Search Report issued by the European Patent Office issued in connection with European Patent Application No. 19850544.8 (11 pages).

Office Action dated May 5, 2021, issued in connection with U.S. Appl. No. 16/436,284 (13 pages).
Office Action dated Nov. 29, 2021, issued in connection with U.S. Appl. No. 16/436,284 (14 pages).
Hacihaliloglu, et al., "Projection-Based Phase Features for Localization of a Needle Tip in 2D Curvilinear Ultrasound," Med. Image. Comput. Assist. Interv. Springer LNCS, 9349, pp. 347-354, (2015) (8 pages).
Xiang, et al., "PoseCNN: A Convolutional Neural Network for 6D Object Pose Estimation in Cluttered Scenes," arXiv: 1711.001993, May 26, 2018 (10 pages).
Qiu, et al., "Phase Grouping-Based Needle Segmentation in 3-D Trans-rectal Ultrasound-Guided Prostate Trans-Perineal Therapy," Ultrasound in Med. & Biol., vol. 40, No. 4, p. 804-816 (2014) (13 pages).
Barva, et al., "Parallel Integral Projection Transform for Straight Electrode Localization in 3-D Ultrasound Images," EEE Transactions on Ultrasonics, Ferroelectrics, and Frequency Control, vol. 55, No. 7, pp. 1559-1569, Jul. 2008 (11 pages).
Ayvali, et al., "Optical Flow-Based Tracking of Needles and Needle-Tip Localization Using Circular Hough Transform in Ultrasound Images," Ann Biomed Eng, 43(8), pp. 1828-1840, Aug. 2015 (23 pages).
Beigi, et al., "Needle Trajectory and Tip Localization in Real-Time 3-D Ultrasound Using a Moving Stylus," Ultrasound in Medicine & Biology, vol. 41, No. 7, pp. 2057-2070, (2015) (14 pages).
Arif, et al., "Needle Tip Visibility in 3D Ultrasound Images," Cardiovasc Intervent Radiol 41(1), pp. 145-152 (2018) (8 pages).
Harmat, et al., "Needle Tip Localization Using Stylet Vibration," Ultrasound in Med. & Biol., vol. 3, No. 9, pp. 1339-1348 (2006) (10 pages).
Stolka, et al., "Needle Guidance Using Handheld Stereo Vision and Projection for Ultrasound-Based Interventions," Med Image Comput Comput Assist Interv, 17(Pt.2), p. 684-691 (2014) (12 pages).
Kuang, et al., "Modelling and Characterization of a Ultrasound-Actuated Needle for Improved Visibility in Ultrasound-Guided Regional Anaesthesia and Tissue Biopsy," Ultrasonics, 69, pp. 38-46 (2016) (9 pages).
Uhercik, et al., "Model Fitting Using RANSAC for Surgical Tool Localization in 3-D Ultrasound Images," IEEE Transactions on Biomedical Engineering, vol. 57, No. 8, pp. 1907-1916, Aug. 2010, (10 pages).
Torr, et al., "MLESAC: A New Robust Estimator with Application to Estimating Image Geometry," Computer Vision and Image Understanding, 78(1), pp. 138-156 (2000) (19 pages).
Fong, et al., "LSMR: An Iterative Algorithm for Sparse Least-Squares Problems," arXiv: 1006.0758v2, Jun. 10, 2011 (21 pages).
Pourtaherian, et al., "Improving Needle Detection in 3D Ultrasound Using Orthogonal-Plane Convolutional Networks," MICCAI Part 2, LNCS 10434, pp. 610-618, (2017) (9 pages).
Moore, et al., "Image Guidance for Spinal Facet Injections Using Tracked Ultrasound," Med Image Comput Comput Assist Interv. Part 1, LNCS 5761, pp. 516-523 (2009) (8 pages).
Dalal, et al., "Histograms of Oriented Gradients for Human Detection," Proceedings of the 2005 IEEE Computer Society Conference on Computer Vision and Pattern Recognition (CVPR 2005) (8 pages).
Ren, et al., "Faster R-CNN: Towards Real-Time Object Detection with Region Proposal Networks," ArXiv:1506.01497v3, Jan. 6, 2016 (14 pages).
Afonso, et al., "Fast Image Recovery Using Variable Splitting and Constrained Optimization," IEEE Transactions on Image Processing, vol. 19, No. 9, pp. 2345-2356, Sep. 2010 (12 pages).
Agarwal, et al., "Facial Key Points Detection Using Deep Convolutional Neural Network—NaimishNet," arXiv:1710.00977v1, Oct. 3, 2017 (7 pages).
Zhao, et al., "Evaluation and Comparison of Current Biopsy Needle Localization and Tracking Methods Using 3D Ultrasound," Ultrasonics 73, pp. 206-220 (2017) (15 pages).
Mwikirize, et al., "Enhancement of Needle Tip and Shaft from 2D Ultrasound Using Signal Transmission Maps," Medical Image Computing and Computer-Assisted Intervention—MICCAI 2016, Part 1, LNCS 9900, pp. 362-369 (2016) (8 pages).

(56) References Cited

OTHER PUBLICATIONS

Hatt, et al., "Enhanced Needle Localization in Ultrasound Using Beam Steering and Learning-Based Segmentation," Computerized Medical Imaging and Graphics 41, pp. 46-54 (2015) (9 pages).
Hakime, et al., "Electromagnetic-Tracked Biopsy Under Ultrasound Guidance: Preliminary Results," Cardiovasc Intervent Radiol 35(4), pp. 898-905 (2012) (8 pages).
Krucker, et al., "Electromagnetic Tracking for Thermal Ablation and Biopsy Guidance: Clinical Evaluation of Spatial Accuracy," J Vase Interv Radiol,18(9), pp. 1141-1150, Sep. 2007 (22 pages).
Meng, et al., "Efficient Image Dehazing with Boundary Constraint and Contextual Regularization," 2013 IEEE International Conference on Computer Vision, pp. 617-624 (8 pages).
Mwikirize, et al., "Convolution Neural Networks for Real-Time Needle Detection and Localization in 2D Ultrasound," International Journal of Computer Assisted Radiology and Surgery 13(5), pp. 647-657 (2018) (11 pages).
Kirsch, "Computer Determination of the Constituent Structure of Biological Images," Computers and Biomedical Research. 4, pp. 315-328 (1971) (14 pages).
Beigi, et al., "CASPER: Computer-Aided Segmentation of Imperceptible Motion-A Learning-Based Tracking of an Invisible Needle in Ultrasound," Int J Cars, 12, pp. 1857-1866 (2017) (10 pages).
Zhao, et al., "Biopsy Needle Localization and Tracking Using ROI-RK Method," Abstract and Applied Analysis (2014) (8 pages).
Zhou, et al., "Automatic Needle Segmentation in 3D Ultra-Sound Images Using 3D Improved Hough Transform," Proceedings of SPIE Medical Imaging, vol. 6918, pp. 691821-1-691821-9 (2008) (10 pages).
Zhao, et al., "Automatic Needle Detection and Tracking in 3D Ultrasound Using an ROI-Based RANSAC and Kalman Method," Ultrasonic Imaging 35(4), pp. 283-306 (2013) (24 pages).
Arif, et al., "Automatic Needle Detection and Real-Time Bi-Planar Needle Visualization During 3D Ultrasound Scanning of the Liver," Medical Image Analysis 53, pp. 104-110 (2019) (7 pages).
Chan, et al., "Aspects of Total Variation Regularized L1 Function Approximation," Technical Report, University of California at Los Angeles (2004) (22 pages).
Chan, et al., "An Augmented Lagrangian Method for Total Variation Video Restoration," IEEE Transactions on Image Processing, vol. 20, No. 11, pp. 3097-3111, Nov. 2011 (15 pages).
Litjens, et al., "A Survey on Deep Learning in Medical Image Analysis," Medical Image Analysis, 42, pp. 60-88 (2017) (29 pages).
Lu, et al., "A New Sensor Technology for 2D Ultrasound-Guided Needle Tracking," Med Image Comput Comput Assist Interv, Part 2, LNCS 8674, pp. 389-396 (2014) (8 pages).
Redmon, et al., "Yolo9000: Better, Faster, Stronger," arXiv:1612.08242v1, Dec. 25, 2016 (9 pages).
Miura, et al., "Visibility of Ultrasound-Guided Echogenic Needle and Its Potential in Clinical Delivery of Regional Anesthesia," Tokai J Exp Clin Med., vol. 39, No. 2, pp. 80-86 (2014) (7 pages).
Korbe, et al., "Ultrasound-Guided Interventional Procedures for Chronic Pain Management," Pain Management, 5(6), pp. 466-482 (2015) (18 pages).
Karamalis, et al., "Ultrasound Confidence Maps Using Random Walks," Medical Image Analysis 16 pp. 1101-1112 (2012) (12 pages).
Osher, "The Split Bregman Method for L1-Regularized Problems," SIAM Journal on Imaging Sciences, Jan. 2009 (29 pages).
Zveringham, et al., "The PASCAL Visual Object Classes (VOC) Challenge," Int J Comput Vis 88: pp. 303-338 (2010) (36 pages).
Elsharkawy, et al.,"The Infiniti Plus Ultrasound Needle Guidance System Improves Needle Visualization During the Placement of Spinal Anesthesia," Korean Journal of Anesthesiology, vol. 69, No. 4, pp. 417-419, Aug. 2016 (3 pages).
Beigi, et al., "Spectral Analysis of the Tremor Motion for Needle Detection in Curvilinear Ultrasound Via Spatiotemporal Linear Sampling," Int J Comput Assist Radiol Surg, 11, pp. 1183-1192 (2016) (10 pages).
Office Action dated Apr. 15, 2021, issued in connection with U.S. Appl. No. 16/436,284 (15 pages).

\* cited by examiner

COMPUTER VISION SYSTEMS AND METHODS FOR REAL-TIME LOCALIZATION OF NEEDLES IN ULTRASOUND IMAGES

RELATED APPLICATIONS

This application is a U.S. National Phase Application under 35 U.S.C. 371 of International Application No. PCT/US2019/046364 filed Aug. 13, 2019, which was published on Feb. 20, 2020, under International Publication Number WO 2020/036968, which claims the benefit of priority to U.S. Provisional Patent Application Ser. No. 62/718,090 filed on Aug. 13, 2018, the entire disclosures of which these applications are hereby expressly incorporated by reference.

BACKGROUND

Technical Field

The present disclosure relates generally to the field of computer vision technology. More specifically, the present disclosure relates to computer vision systems and methods for real-time localization of needles in ultrasound images.

RELATED ART

Minimally invasive procedures such as regional anesthesia and interventional oncology involve the insertion of a needle toward target anatomy. In practice, image guidance is used to improve targeting accuracy. Of all imaging modules, ultrasound imaging is ubiquitously used due to real-time, low-cost and radiation-free capabilities. However, with conventional 2D ultrasounds, aligning the needle with the ultrasound imaging plane at steep angles and deep insertions is difficult.

Real-time and accurate localization of hand-held needles is vital for the success of percutaneous ultrasound guided interventions such as biopsies and regional anesthesia. However, needle localization is a challenge when the needle shaft and tip are not fully visible. This could arise from difficulty aligning the needle with the scan plane and reflection of the ultrasound signal from the needle away from the transducer. The ensuing targeting errors may reduce procedure efficacy.

A two-dimensional (2D) ultrasound is the standard imaging modality used for guiding percutaneous interventions in clinics due to its real-time non-radiation-based imaging functionality. In a normal work-flow, a radiologist advances the needle by hand and manipulates an ultrasound transducer, while concurrently observing needle motion vis-a-vis body anatomy. Prior art systems for improving needle localization during these procedures require the needle shaft and tip to have a high intensity, which is often not the case. Moreover, many prior art solutions involve computationally expensive processing routines. In addition, many of these solutions do not localize bending needles, which is a necessary feature as needles need to bend around critical anatomical structures in some procedures. Some prior art methods are not desirable because they involve computationally complex processing for computing motion vectors and are sensitive to noise and brightness variation. Moreover, prior art solutions cannot localize needles that are not wholly visible.

Therefore, there is a need for computer vision systems and methods for real-time localization of needles in ultrasound images, which is fast and accurate and can localize needles which cannot be seen. These and other needs are addressed by the computer vision systems and methods of the present disclosure.

SUMMARY

Computer vision systems and methods for real-time localization of a needle in an ultrasound video are provided. The method includes a step of receiving at a processor a plurality of frames from the ultrasound video. The method also includes the step of identifying by the processor one of the plurality of frames as a background image and a frame adjacent to the background image as a current image. The method further includes the step of performing by the processor a bitwise complement operation on the background image to generate a complement image. Moreover, the method includes the step of performing by the processor a pointwise logical AND operation on the complement image and the current image to identify the location of the needle.

A system for real-time localization of a needle in an ultrasound video is provided. The system includes a memory having computer instructions stored thereon, which when executed, causes a processor to perform a number of steps. The first step includes receiving a plurality of frames from the ultrasound video. The second step includes identifying one of the plurality of frames as a background image and a frame adjacent to the background image as a current image. The third step includes performing by the processor a bitwise complement operation on the background image to generate a complement image. The fourth step includes performing a pointwise logical AND operation on the complement image and the current image to identify the location of the needle.

BRIEF DESCRIPTION OF THE DRAWINGS

The foregoing features of the invention will be apparent from the following Detailed Description of the Invention, taken in connection with the accompanying drawings, in which.

DETAILED DESCRIPTION

Figure 1:
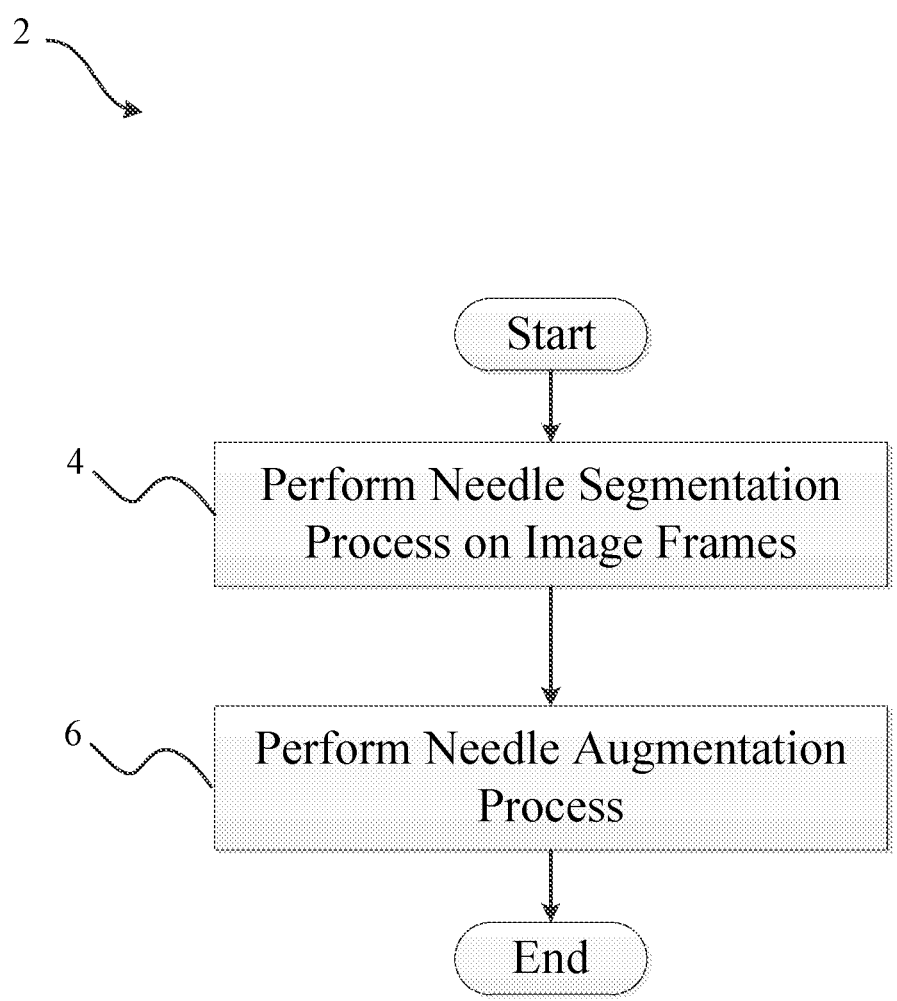
FIG. 1 is a flowchart illustrating processing steps for localizing a needle in ultrasound images.

The present disclosure relates to computer vision systems and methods for real-time localization of needles in ultrasound images as described in detail below in connection with FIGS. 1-15.

The systems and methods of the present disclosure provide solutions for real-time and accurate localization of needles (even if they are invisible) in an ultrasound scan. The systems and methods use a foreground detection algorithm for automatic needle segmentation from consecutive ultrasound image frames. The needle tip is then localized by solving a spatial total variation regularization problem using, for example, a Split Bregman method. The systems and methods of the present disclosure are not limited to the Split Bregman method as other regularization methods can be used on the data. For example, deep learning and reinforcement learning can be performed on ultrasound datasets to model the appearance of a needle tip in an ultrasound image thereby improving needle tip detection and reducing irrelevant background noise. Also, Split Bregman can be a general categorical formulation of the method, and other applications (e.g., noise model, sub-problem derivation, and solution, parameter optimization) can be specific to the moving device localization problem.

Although the systems and methods of the present disclosure provide for the localization of a needle, the systems and methods are not limited to localizing needles. In particular, the systems and methods can be used to localize any type of medical device or surgical instrument, including, but not limited to, forceps, stainless steel rods with conical tips, catheters, guidewires, radio frequency ablation electrodes, balloons (during angioplasty/stenting procedures), or any other medical devices. Moreover, although the systems and methods of the present disclosure provide for localization of any medical device in an ultrasound video, any type of imaging modalities can be used. In particular, the systems and methods of the present disclosure can localize any type of medical instrument in any type of video format or file because the logical differencing approach and Split Bregman method is compatible with any type of video.

The systems and methods of the present disclosure accomplish at least the following goals. First, the systems and methods perform needle segmentation based on a dynamic background model that can account for noise in an ultrasound. Second, the systems and methods can apply the Split-Bregman approach in a unique way to solve a spatial total variation (TV) problem for needle tip enhancement in 2D ultrasounds. Third, the systems and methods can accurately localize a needle tip in a computationally fast way with a high degree of accuracy. Fourth, the systems and methods can localize a needle for in-plane and out-of-plane insertions without the need for full needle visibility. Fifth, the systems and methods can localize bending needles since as there is no need for the needle to appear as a linear feature in the ultrasound image. Sixth, the systems and methods can be utilized in a smart computer assisted interventional system to facilitate needle localization in the presence of artifacts from anatomical features and other instruments.

The methods and systems of the present disclosure can be used with hand-held 2D ultrasound probes, during in-plane and out-of-plane needle insertion. For in-plane insertion, the method can handle insertion angles greater than 40°, but can also work with shallower angles. The method detects scene changes caused by needle motion in the ultrasound image scene. In each frame of the ultrasound sequence, the needle tip can be treated as the foreground, while the rest of the image can be designated as background data. The method does not require prior knowledge of the needle insertion side or angle. The needle localization process includes two phases: 1) needle segmentation from logical differencing of a dynamic reference ultrasound frame from the ultrasound frame of interest, and 2) needle tip augmentation in the ultrasound image with the segmented needle.

In a dynamic background model, the background of each frame (k) is modeled as the previous frame (k−1), based on logical differencing. The enhanced image is based on a point-wise operator of the complement of the background and the image (what is NOT in the k−1 frame but in the k−1 frame). This makes it possible to identify the objects that have moved between the two frames: the needle tip. To ensure that movement actually occurs between the two frames, the correlation coefficient of the background and current frame is calculated. The image is only used for tip localization if the difference exceeds a threshold.

FIG. 1 is a flowchart illustrating processing steps 2 for localizing a needle in an ultrasound video sequence. In step 4, the process performs needle segmentation, which will be explained in greater detail below. In step 6, the process performs needle augmentation which will be explained in greater detail below.

Figure 2:
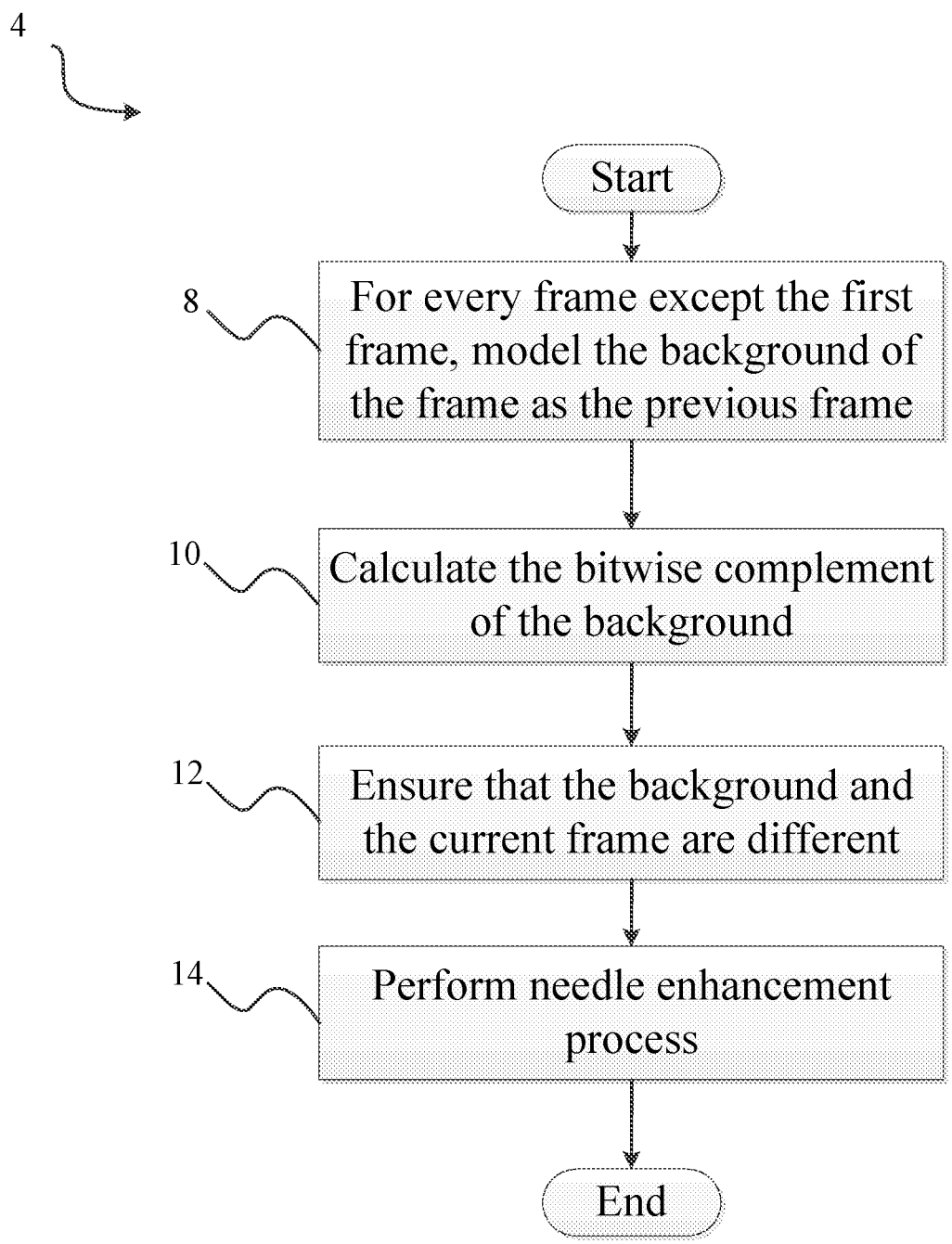
FIG. 2 is a flowchart illustrating processing steps for a performing needle segmentation process of FIG. 1.

FIG. 2 is a flowchart illustrating processing steps 4 for performing needle segmentation as discussed in connection with FIG. 1. Consider an ultrasound frame sequence with temporal continuity, represented by the function $p(x, y, t)$, where t denotes the position in the time sequence and $(x, y)$ are the spatial coordinates. The process 4 uses a dynamic background model which quickly adapts to changes in the ultrasound scene by employing a logical differencing approach for adjacent frames. In step 8, for the first frame, the background can be denoted as: $b(x, y, t_0)=p(x, y, t_0)$, and for all subsequent frames, the background is modeled as the previous frame in the sequence (which can be written as $b(x, y, t_n)=p(x, y, t_{n-1})$). In step 10, the method can then calculate the bitwise complement of the background image. Considering only spatial variation, for $b(x, y)=(x, y)|b(x, y)\neq 0$, the complement is $b^c(x, y)=(x, y) \in Z \mid (x, y) \in b(x, y)$. In step 12, the method can ensure that the background and the current frame are different. In step 14, for any current frame $p(x, y)$, the needle enhanced image equation is given by:

$$q(x,y)=b^c(x,y) \wedge p(x,y). \qquad \text{Equation 1}$$

where ∧ denotes a point-wise AND logical operation. The needle enhancement equation yields only the objects in the ultrasound that moved between two successive frames, and thus gives an enhanced current needle tip location. The method can account for concurrent tissue movement surrounding the needle tip by taking into account collocated motion of the tissue and tip to be more significant than any other motion. Depending on the needle visibility profile, q(x, y) can also contain an enhanced shaft. Since a short interval exists between successive frames, the method can minimize the effect of intensity changes in the rest of the ultrasound image, which leads to stable needle detection. In some cases, insignificant changes in needle motion will lead to an all zeros q(x, y). This is expected since in typical ultrasound imaging (greater than 20 frames per second), the needle tip will not be at a different location in each frame, even with continuous motion. Before applying the needle enhancement equation, the method can ensure that b(x, y), the background, and p(x, y), the current frame, are different (as discussed with regard to step 12). Accordingly, the method can calculate the correlation coefficient, p, between the two images, and increment to the next frame while maintaining the current frame position if p exceeds a predetermined threshold.

The output of the needle enhancement equation in step 14 of FIG. 2, r(x, y), can also contain artifacts that do not belong to the needle. This is expected due to brightness variations in the ultrasound images, and the motion of tissues/organs that do not correspond to needle tip motion. Accordingly, the method of the present disclosure can enhance the output r(x, y) such that the needle tip distinctively has the highest appearance. This can be thought of as an image restoration (de-noising) problem. The method can formulate a model as follows: r(x, y)=e(x, y)+n(x, y). This model can represent a sum of two components: the desired needle enhanced image e(x, y) and unwanted artifacts (noise), n(x, y). The desired needle enhanced component e(x, y) can be a function of bounded variation. Moreover, the images can be represented by vectors. The image restoration model becomes:

$$r = e + n \quad \text{Equation 2}$$

where $e \in \mathbb{C}^{mn \times 1}$ is the desired enhanced image (of size m×n), $r \in R^{mn \times 1}$ is the corrupted image, while $n \in R^{mn \times 1}$ is the noise. In this notation, r, e, and n are vectors containing all the pixel values in the respective image matrices in lexicographic order. The vector n can represent stochastic or deterministic noise. Since pixels in the segmented image have spurious detail and possibly high total variation, the method can formulate a total variation regularization problem in the following form:

$$\min_{e} \frac{\lambda}{2}\|r - e\|_2^2 + \|e\|_{TV}, \quad \text{Equation 3}$$

where $\lambda$ is a regularization parameter and $\|e\|_{TV} = \|D_x e\|_1 + \|D_y e\|_1$ is the anisotropic total variation norm, defined by $D_x$ and $D_y$, which are the spatial first-order forward finite difference operators along the horizontal and vertical directions respectively. The equation representing the total variation problem above can be a constrained formulation of a non-differentiable optimization problem. This problem can be efficiently solved with the Split Bregman approach, in which the main problem is reduced to a sequence of unconstrained optimization problems and variable updates. We first transform the equation representing the total variation problem into a constrained equivalent problem by introducing intermediate variables v and w, in the following equation:

$$\min_{v,\omega,e} \frac{\lambda}{2}\|r - e\|_2^2 + \|v\|_1 + \|\omega\|_1 \quad \text{Equation 4}$$

$$\text{subject to} \quad v = D_x e$$

$$\omega = D_y e$$

The method can then weakly enforce the constraints in the above equation by introducing quadratic penalties, and strictly enforce the constraints by applying the Bregman iteration as follows:

$$\min_{v,\omega,e} \frac{\lambda}{2}\|r - e\|_2^2 + \|v\|_1 + \|\omega\|_1 + \frac{v}{2}\|v - D_x e - b_1\|_2^2 + \frac{v}{2}\|\omega - D_y e - b_2\|_2^2, \quad \text{Equation 5}$$

where v is an additional regularization parameter, and the values of $b_1$ and $b_2$ are determined through Bregman iteration. Now a series of three sub-problems can be written as the following equations:

$$\min_{v} \quad \|v\|_1 + \frac{v}{2}\|v - D_x e - b_1\|_2^2 \quad \text{Equation 6}$$

$$\min_{\omega} \quad \|\omega\|_1 + \frac{v}{2}\|\omega - D_y e - b_2\|_2^2 \quad \text{Equation 7}$$

$$\min_{e} \frac{\lambda}{2}\|r - e\|_2^2 + \frac{v}{2}\|v - D_x e - b_1\|_2^2 + \frac{v}{2}\|\omega - D_y e - b_2\|_2^2 \quad \text{Equation 8}$$

Equations 6 and 7 can decouple over space and can have closed-form solutions as vectorial shrinkages given by the following equations:

$$v = \text{sign}(D_x e + b_1) \times \max\left\{|D_x e + b_1| - \frac{1}{v}, 0\right\} \quad \text{Equation 9}$$

$$\omega = \text{sign}(D_y e + b_2) \times \max\left\{|D_y e + b_2| - \frac{1}{v}, 0\right\}$$

From the third sub-problem equation 8 above, the following equation can be derived:

$$e[\lambda I - v\{D_x^T D_x + D_y^T D_y\}] = \lambda r + v D_x^T(v - b_1) + v D_y^T(w - b_2) \quad \text{Equation 10}$$

Equation 10 can be solved using an iterative least squares solver by initializing $b_1$ and $b_2$ to zero and updating these variables after each Bregman iteration: $b_1^{i+1} = b_1^i + D_x e - v$, $b_2^{i+1} = b_2^i + D_y e - w$.

Figure 3:
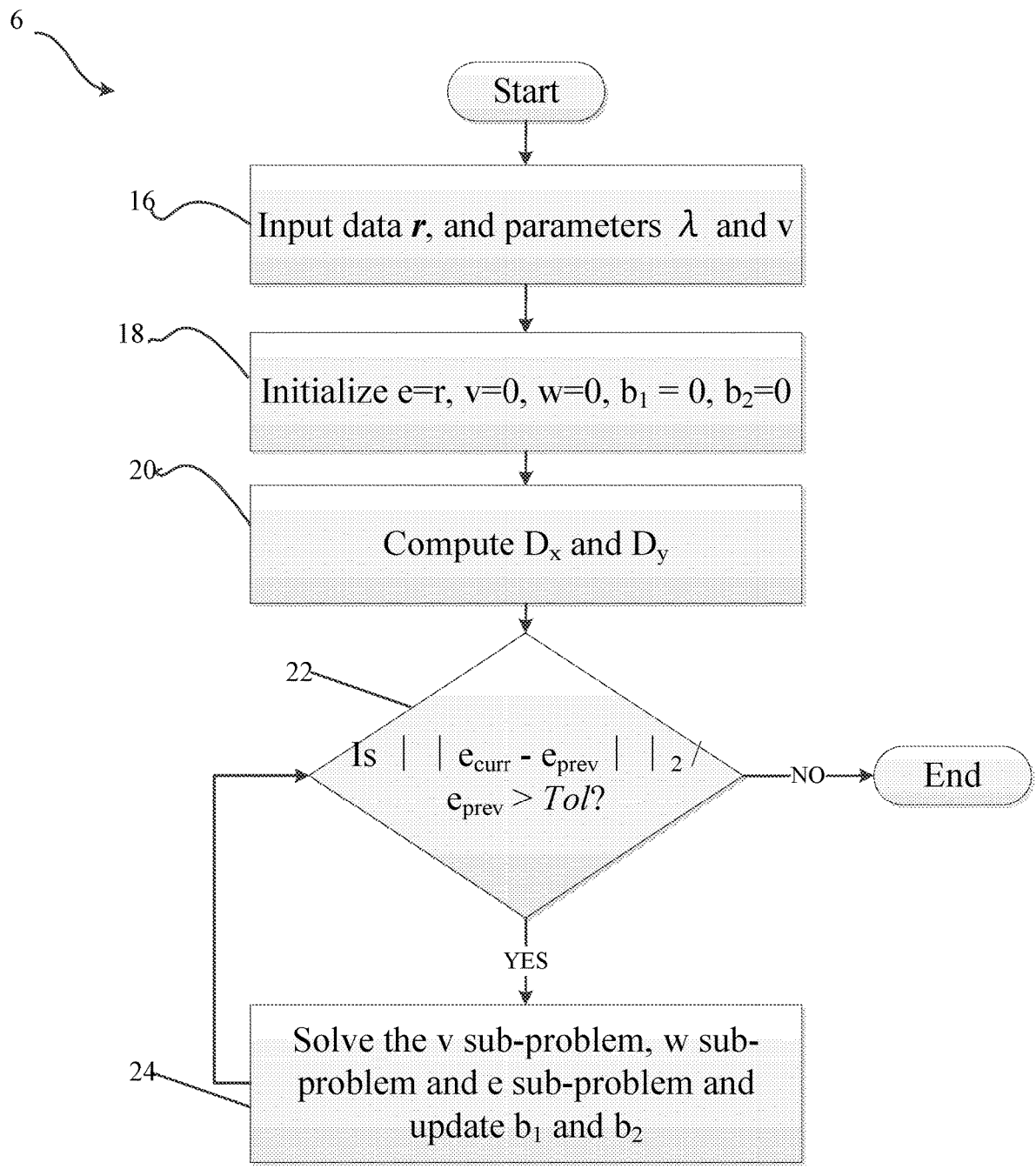
FIG. 3 is a flowchart illustrating processing steps for performing a needle augmentation process of FIG. 1.

FIG. 3 is a flowchart illustrating the process 6 for needle augmentation as discussed above in connection with FIG. 1, in greater detail. The process 6 can be implemented in accordance with the above equations and disclosure discussed above in connection with performing needle enhancement. In step 16, the method can input data r and parameters $\lambda$ and v. In step 18, the method can initialize the following variables: e=r, v=0, w=0, $b_1$=0, $b_2$=0. In step 20, the method can compute $D_x$ and $D_y$ in accordance with the above equations. In step 22, the method can make a determination as to whether $\|e_{curr} - e_{prev}\|_2 / e_{prev}$ is greater than the Tol variable (a threshold). If a positive determination is made, the method can proceed to step 24 in which v sub-problem, the w sub-problem and the e sub-problem are solved, and $b_1$ and $b_2$ are updated. If a negative determination is made in step 22, the method ends.

Data acquisition and experimental validation will now be explained in greater detail. 2D B-mode ultrasound data was collected using two imaging systems: SonixGPS (Analogic Corporation, Peabody, Mass., USA) with a hand-held C5-2/60 curvilinear probe, and 2D hand-held wireless ultrasound (Clarius C3, Clarius Mobile Health Corporation, Burnaby, British Columbia, Canada). Experiments were performed on a freshly excised bovine tissue, and a porcine shoulder phantom, with insertion of a 17 gauge (1.5 mm diameter, 90 mm length) Tuohy epidural needle (Arrow International, Reading, Pa., USA) and a 22 gauge (0.7 mm diameter, 90 mm length) spinal Quincke-type needle (Becton, Dickinson and Company, Franklin Lakes, N.J., USA). In-plane insertion was performed at 40°-70° and the needle was inserted up a depth of 70 mm. 30 (15 in-plane, 15 out-of-plane) sequences of ultrasound images, each containing more than 100 frames were collected.

The method of the present disclosure was implemented in MATLAB 2017b on a 3.6 GHz Intel® Core™ i7 CPU, 16 GB RAM Windows personal computer. The present disclosure is not limited to this personal computer but it can be a good choice when the sub-problems of the method discussed above converge quickly and are numerically well conditioned. The variable v can, in some cases, be neither be too large or too small. As an example only, v=2 can be a good value, but in some cases, the de-noising output may not be sensitive to that specific value. The parameter λ can affect the balance between removing noise and preserving image content. Although, in some cases, it is preferable to use a value that matches the variance of the noise, the noise characteristics of r(x, y) are unknown. Accordingly, a value of λ=5 can be used. In some cases, the threshold of the correlation coefficient for skipping a frame due to insignificant motion can be 1. A value of p>0.995 was feasible for most of the ultrasound data. Throughout the validation experiments, these values were not changed. Performance of the method was evaluated by comparing the automatically detected tip location to the ground truth determined by an expert sonographer. Tip localization accuracy was determined from the Euclidean distance between the two measurements.

The results and analysis will now be explained in greater detail. With regard to quantitative results, the method is computationally efficient, and achieves convergence in less than 10 iterations, with Tol=$\|e_{curr}-e_{prev}\|_2/e_{prev}$ is less than or equal to $10^{-3}$. However, to save computational cost, the enhancement algorithm was run for only 3 iterations (0.06 s), and achieves sufficient tip enhancement. The total computation time is 0.08 s for each ultrasound frame: 0.01 s for segmentation and 0.06 s for enhancement and localization. This represents a substantial improvement in simplifying computational complexity of the needle localization problem. Error statistics for in-plane and out-of-plane needle insertion are shown in Table 1 below. Table 1 shows mean error with a 95% confidence interval. The term "RMS" means Root Mean Square. The term "SD" means Standard Deviation. All values shown in Table 1 are in mm. In some cases, localization for in-plane insertions can be more accurate than that for in-plane insertions. The overall tip localization is 0.50±0.02 mm

TABLE 1

| Needle insertion | Number of images | Mean | SD | RMS | Maximum |
|---|---|---|---|---|---|
| In-plane | 650 | 0.46 ± 0.02 | 0.27 | 0.54 | 0.95 |
| Out-of-plane | 380 | 0.56 ± 0.03 | 0.29 | 0.63 | 1.20 |
| Overall | 1030 | 0.50 ± 0.02 | 0.28 | 0.58 | 1.20 |

Figure 4:
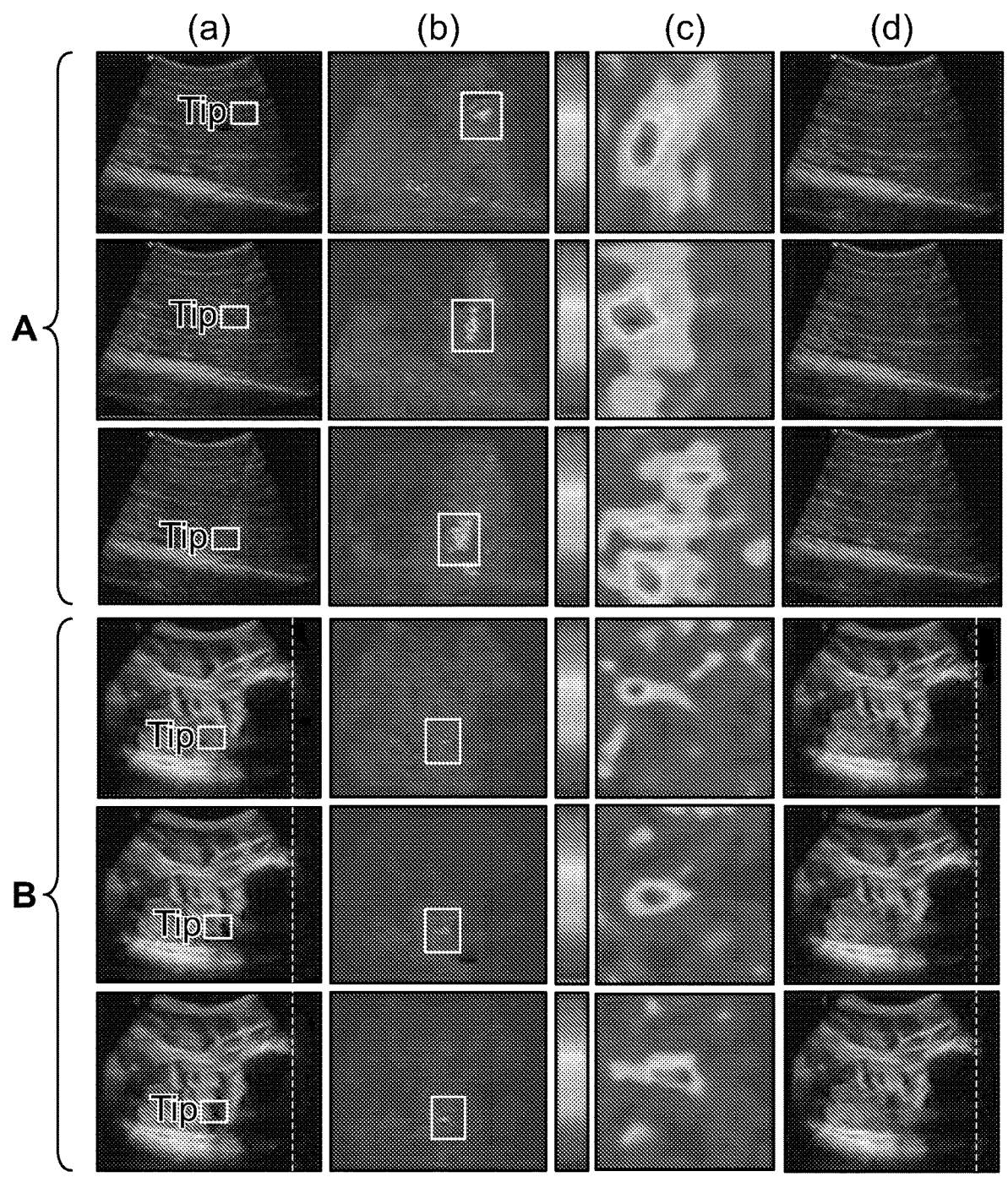
FIG. 4 shows needle localization results for consecutive frames from both in-plane and out-of-plane insertion of a 17 gauge needle.

With regard to qualitative results, FIG. 4 shows needle localization results for consecutive frames from both in-plane and out-of-plane insertion of a 17 gauge needle. In both cases, the needle tip is accurately localized. For out-of-plane needles, the temporal window for needle tip visibility is limited, but the present method can account for this limitation by tracking small perturbations of the needle tip close to the target. As can be seen in FIG. 4, needle localization in 3 consecutive frames is shown with rows (A) illustrating in-plane insertion and rows (B) illustrating out-of-plane insertion of the 17 gauge needle. Column (a) illustrates an original image showing an annotated expert-localized tip. Column (b) illustrates a needle enhanced image, e(x, y) (color coded), in which the rectangle surrounds the localized tip. Column (c) illustrates a zoomed in region of interest from column (b) containing the needle tip, and which also shows a colorbar for illustrating where the tip has the highest intensity in the image. Column (d) illustrates the automatically localized tip (shown as red dot) overlaid on the original image. As can be seen, the present method achieves accurate localization for both in-plane and out-of-plane needles.

Figure 5A:
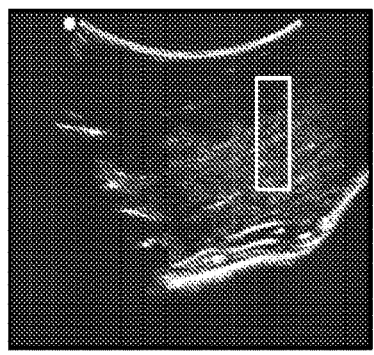
FIGS. 5A-5C show needle localization results for in-plane insertion of a 22 gauge needle.
Figure 5B:
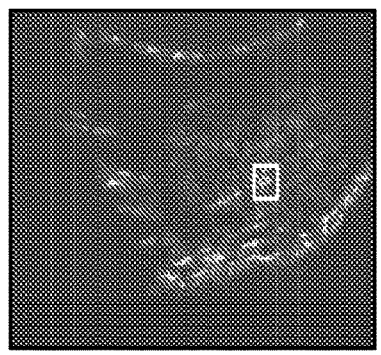
Figure 5C:
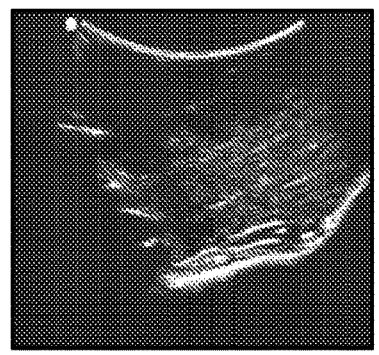

FIGS. 5A-5C show needle localization results for in-plane insertion of a 22 gauge needle. Note that in the unaltered image, the needle tip and shaft are inconspicuous because this needle is thinner, and as a result, it reflects less of an ultrasound signal back to the transducer. Despite these challenges, the present method accurately localizes the tip. FIG. 5A shows an original image in which the annotated region contains the needle trajectory. As can be seen, the tip location is difficult to discern by the expert. FIG. 5B shows a needle enhanced image, e(x, y) (color coded) in which a rectangle surrounds the localized tip (the highest intensity in the image). FIG. 5C shows the automatically localized tip (red dot) overlaid on original image.

The method of the present disclosure provides a novel approach for needle tip localization in 2D ultrasounds suitable for challenging imaging scenarios in which the needle is not continuously visible. The present method provides for the reduction of computational complexity, leading to a processing rate of 12 fps. The present method does not necessitate the needle to appear as a high intensity, continuous linear structure in the ultrasound image. Therefore, both in-plane and out-of-plane needle localization are achieved. A thin 22 gauge needle was used in the experiments to demonstrate the robustness of the present method to localize partially invisible and curved needles. Typically, such thin needles are prone to bending and the shaft has limited visibility, but this problem did not affect the accuracy of tip localization of the present method.

The method can be applied with the needle already in motion so that subsequent dynamics induce detectable scene changes for the algorithm to compute. The method can also overcome issues of probe re-alignment which might cause abrupt intensity changes unrelated to needle movement. Despite all of the above-mentioned issues, the present method provides a real-time method for needle localization in ultrasounds.

Figure 6:
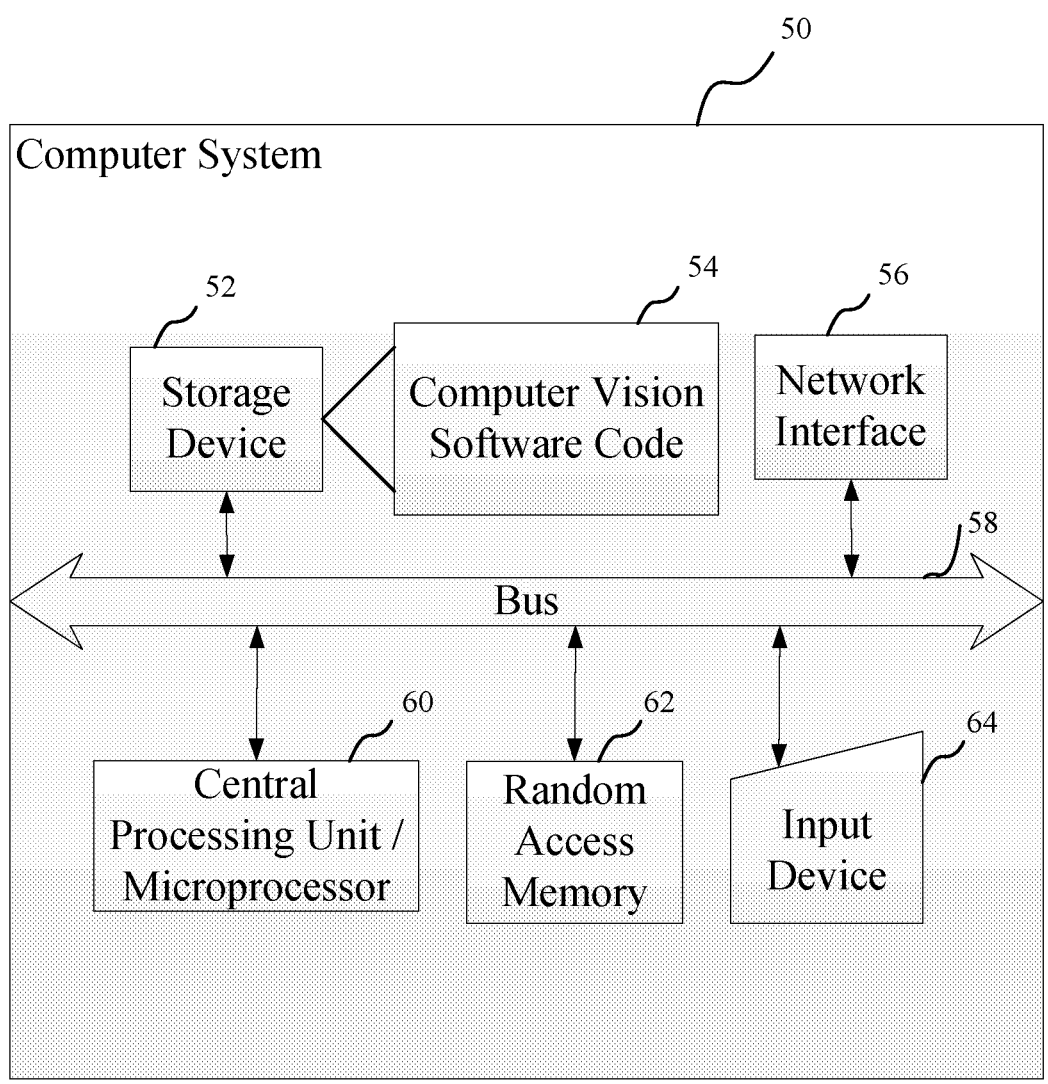
FIG. 6 is a diagram illustrating hardware and software components capable of implementing the systems and methods of the present disclosure.

FIG. 6 is a diagram showing a hardware and software components of a computer system 50 on which the system of the present disclosure can be implemented. The computer system 50 can include a storage device 52, computer vision software code 54, a network interface 56, a communications bus 58, a central processing unit (CPU) (microprocessor) 60, a random access memory (RAM) 62, and one or more input devices 64, such as a keyboard, mouse, etc. The computer system 50 could also include a display (e.g., liquid crystal display (LCD), cathode ray tube (CRT), etc.). The storage device 52 could comprise any suitable, computer-readable storage medium such as disk, non-volatile memory (e.g., read-only memory (ROM), erasable programmable ROM (EPROM), electrically-erasable programmable ROM (EEPROM), flash memory, field-programmable gate array (FPGA), etc.). The computer system 50 could be a networked computer system, a personal computer, a server, a smart phone, tablet computer etc. It is noted that the computer system 50 need not be a networked server, and indeed, could be a stand-alone computer system.

Figure 7:
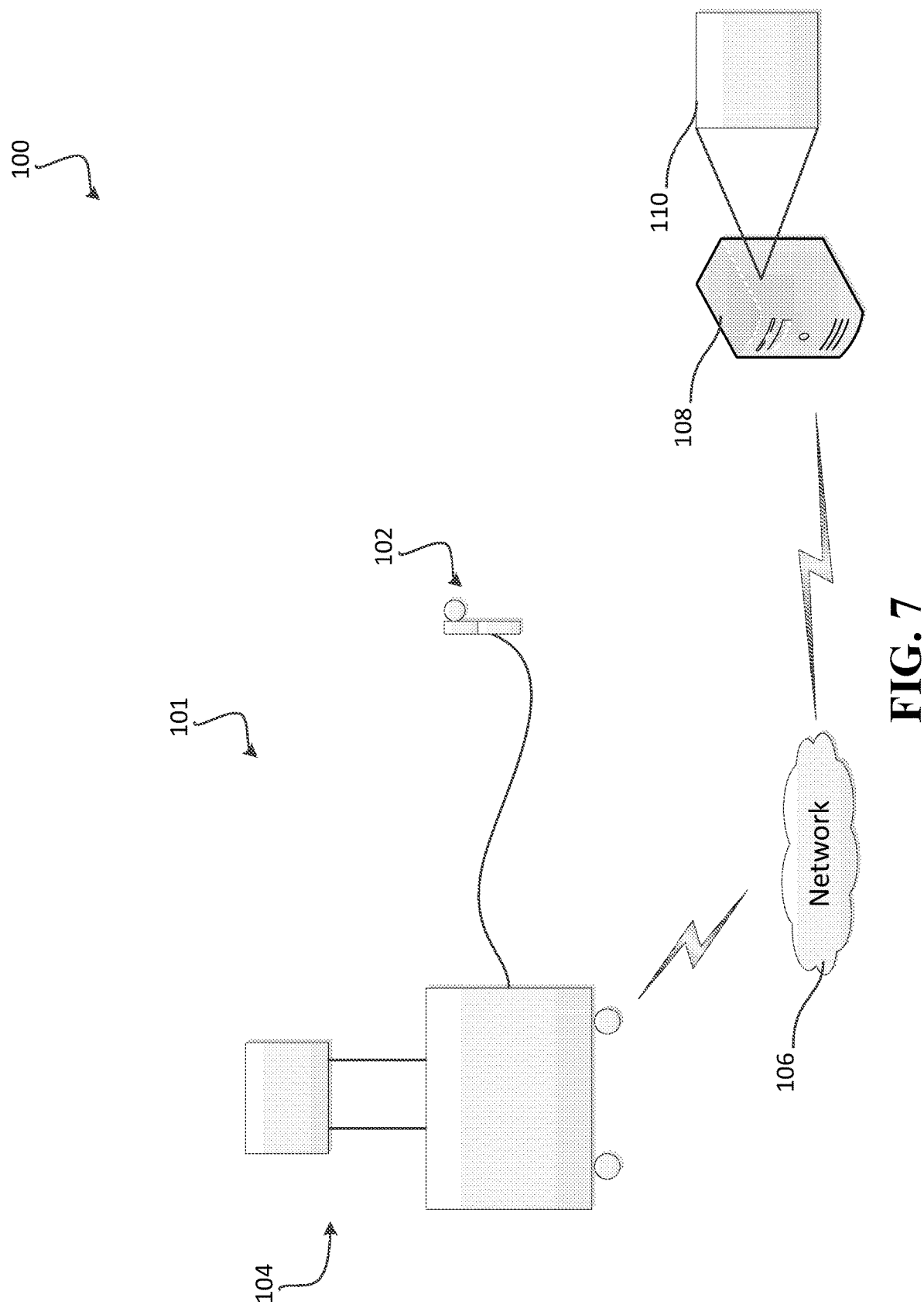
FIG. 7 is a drawing illustrating a system of the present disclosure.

FIG. 7 is a drawing illustrating a system 100 of the present disclosure. The system can include an ultrasound device 101 including an ultrasound receiver 102 and an ultrasound base 104. The ultrasound receiver 102 is a device which can be used by a medical professional for placement on a patient to generate ultrasonic waves and receive a signal for generation of an ultrasonic video/image at the ultrasound base 104. The ultrasound device 101 can transmit data of the ultrasound video over the Internet 106 to a computer system 108 for localizing a medical device in an ultrasound video via a computer vision processing engine 110. It should be noted that the processing engine 110 can be located at the ultrasound base 104 obviating the need for the ultrasound device 101 to send data over the Internet 106 to a remote computer system.

Figure 8:
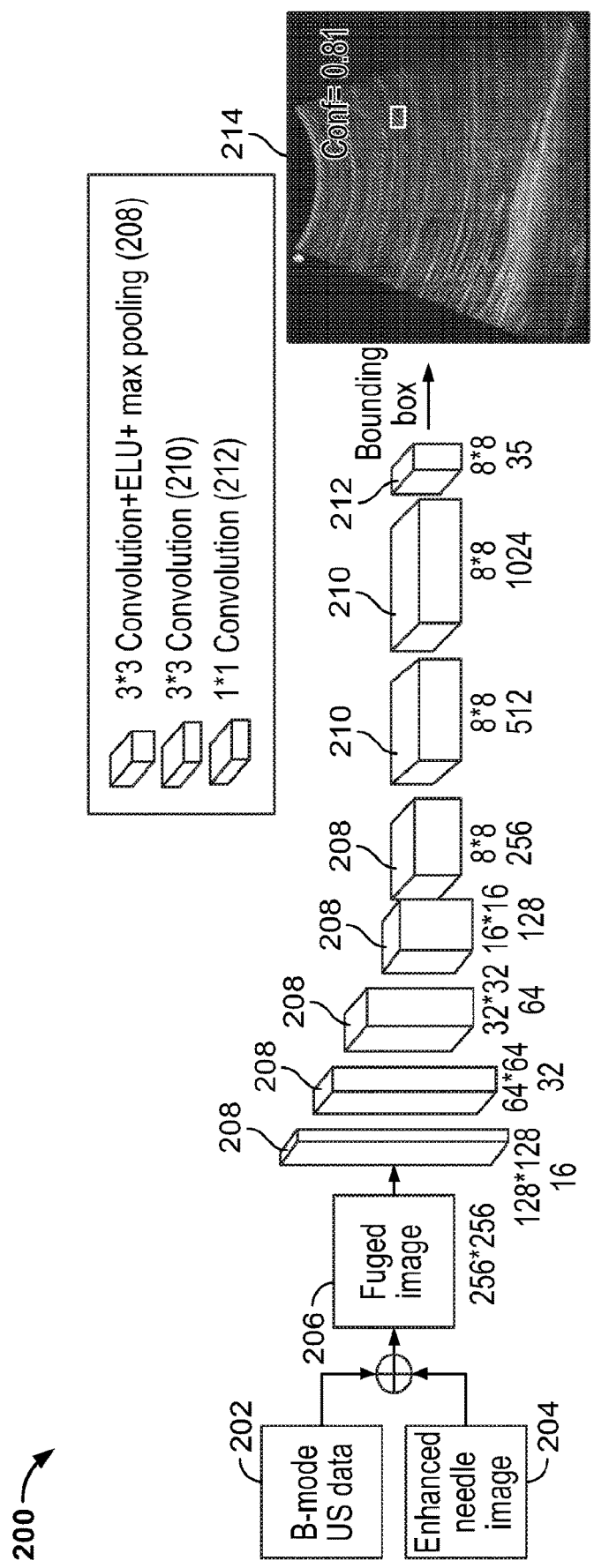
FIG. 8 is a block diagram illustrating another embodiment of the system and method of the present disclosure, wherein a convolutional neural network localizes a needle tip in ultrasound images.

FIG. 8 is a block diagram illustrating another embodiment of the systems and methods of the present disclosure, wherein a convolutional neural network (CNN) localizes a needle tip in ultrasound images. As discussed above, the systems and methods of the present disclosure provide for a needle tip enhanced image e(x, y) in which the needle tip exhibits a high intensity.

It is noted that the needle tip may not always exhibit the highest intensity in the needle tip enhanced image e(x, y) because of needle actuation speed and noise interference. For example, generally, the needle tip will not move in each ultrasound frame because the speed of needle actuation may not match the ultrasound frame rate or the operator may intermittently stop moving the needle. As such, it is necessary to identify frames in which significant motion has not occurred. In addition, despite the above discussed needle enhancement process, high-intensity interfering artifacts not associated with needle motion could be present. Accordingly, a deep learning framework (e.g., a CNN) can be utilized for efficient needle tip detection.

FIG. 8 illustrates the CNN architecture and is built based on You Only Look Once (YOLO) real time object detection. YOLO is a state of the art single-shot object detection CNN architecture. The framework outputs two-dimensional bounding box predictions consisting of five components: x, y, w, h and η, where (x, y) coordinates represent the center of the bounding box, w and h are the width and the height of the bounding box, respectively, and η is the confidence value that the bounding box contains an object and that the object is the needle tip. As shown in FIG. 8, the CNN consists of B-mode ultrasound data 202, enhanced needle image 204, 256×256 fused image input layer 206, a convolution+exponential linear unit (ELU)+max pooling layer 208, a convolution+ELU layer 210 and a convolution layer 212. The CNN is configured to yield a confidence score 214 indicative of needle tip classification and localization accuracy.

The CNN utilizes eight convolutional layers to further reduce computational complexity toward real-time performance, but of course, other numbers of layers could be utilized. The 256×256 fused image input layer 206 is a pixel-level fusion layer in which the current ultrasound image p(x, y) (obtained from the B-mode ultrasound data 202) and its tip enhanced needle image 204 counterpart e(x, y) are concatenated before being input to the CNN. Since the needle tip is a fine-grained feature, the convolution layers are configured to maintain spatial dimensions of the respective inputs, thus mitigating reduction in resolution. It is noted that CNN neurons at deeper layers may have large receptive fields that can ensure incorporation of image level context pertinent to needle tip appearance.

Uniquely, each of the first seven convolution layers is followed by an Exponential Linear Unit (ELU) activation layer, with $\alpha=0.5$. The ELU provides for activations close to zero mean and unit variance to converge toward zero mean and unit variance even under the presence of noise and perturbations. The first five convolutions layers are followed by a 2×2 max pooling layer with a stride of 2. The CNN model is malleable to any input size and provides for two advantages. First, needle tip features will be learned end to end, thus eliminating the need to explicitly encode them. Second, it is expected that frames where no needle tip has moved will exhibit no detectable features, while the learned CNN model will accurately extract the tip when it is present.

The CNN model can be initialized with weights derived from training on the PASCAL Visual Optic Classes (VOC) dataset. The ground-truth bounding box labels can be defined utilizing an electromagnetic (EM) tracking system and a radiologist experienced in interventional radiology. The ground-truth top location becomes the center of the bounding box (x, y) and the thickness w×h is chosen to be at most 20×20 pixels in all images. It is noted that the CNN model can utilize varying learning rates, batch sizes, training durations and optimizers. For example, the CNN model of FIG. 8 utilizes an initial learning rate of $10^{-4}$, a batch size of 4, a training duration of 60 epochs and an Adam optimizer.

Data acquisition and experimental validation of the CNN model of the present disclosure will now be discussed. To train and evaluate the CNN model, a dataset of two-dimensional B-mode ultrasound images was collected using materials and settings specified in Table 2.

TABLE 2

| Imaging system | Needle type, dimensions and insertion profile | # of videos | Pixel size (mm) |
|---|---|---|---|
| Bovine tissue | | | |
| SonixGPS | 17 G SonixGPS (1.5 mm, 70 mm), IP | 5 | 0.17 |
| | 17 G Tuohy (1.5 mm, 70 mm), IP | 10 | 0.17 |
| | 17 G Tuohy (1.5 mm, 70 mm), OP | 3 | 0.17 |
| | 22 G BD (0.7 mm, 90 mm), IP | 5 | 0.17 |
| | 22 G BD (0.7 mm, 90 mm), OP | 7 | 0.17 |

TABLE 2-continued

| Imaging system | Needle type, dimensions and insertion profile | # of videos | Pixel size (mm) |
|---|---|---|---|
| | Porcine tissue on spine phantom | | |
| Clarius C3 | 17 G SonixGPS (1.5 mm, 70 mm), IP | 5 | 0.24 |
| | 17 G Tuohy (1.5 mm, 70 mm), IP | 5 | 0.24 |
| | 22 G BD (0.7 mm, 90 mm), IP | 5 | 0.24 |
| | 22 G BD (0.7 mm, 90 mm), OP | 5 | 0.24 |

IP in-plane insertion,
OP out-of-plane insertion

Specifically, two imaging systems including the SonixGPS (Analogic Corporation, Peabody, Mass., USA) with a handheld C5-2/60 curvilinear probe and the Clarius C3 two-dimensional handheld wireless ultrasound (Clarius C3, Clarius Mobile Health Corporation, Burnaby, BC, Canada) were used. In addition, experiments were performed on freshly excised bovine tissue, a porcine shoulder phantom and chicken breast, with insertion of a 17 gauge (1.5 mm diameter, 90 mm length) Tuohy epidural needle (Arrow International, Reading, Pa., USA), a 17 gauge SonixGPS vascular access needle (Analogic Corporation, Peabody, Mass., USA) and a 22 gauge spinal Quincke-type needle (Becton, Dickinson and Company, Franklin Lakes, N.J., USA). During experimentation, the probe was handheld. Small amplitude perturbations not associated with needle motion were simulated by manually pressing the probe against the imaging medium and rotating it slightly about its longitudinal axis. Further, the chicken breast was overlaid on a lumbosacral spine model and immersed in a water bath during needle insertion to simulate fluid motion in the imaging medium. Ground-truth needle tip localization data using an EM tracking system (Ascension Technology Corporation, Shelburne, Vt., USA) was collected with the SonixGPS needle. Specifically, in-plane insertion was performed at 40°-70°, and the needle was inserted up a depth of 70 mm Fifty (35 in-plane, 15 out-of-plane) sequences of ultrasound images, each containing more than 400 frames, were collected.

Performance of the CNN model was evaluated by comparing the automatically detected needle tip location (i.e., the center of the detected bounding box) to the ground-truth determined from the EM tracking system for data collected with the SonixGPS needle. For data collected with needles without tracking capability, the ground-truth was determined by a radiologist. The ground-truth needle tip location was determined from intensity changes and tissue deformation (this is more difficult in the real-time clinical setting) by retrospectively inspecting the frame sequences. To account for large EM tracking errors (since the sensor does not reach the needle tip), the radiologist performed manual labeling of the dataset obtained with the SonixGPS needle and compared the EM data with the manual data. The EM system provides annotation on the ultrasound frames which acts as a visual cue to the approximate needle tip location in scenarios where the needle tip intensity is low. The radiologist used this information to label the needle tip. If the difference in needle tip localization was 4 pixels (~0.7 mm) or greater, the localizations were not included in the computation. Needle tip localization accuracy was determined from the Euclidean distance between the ground-truth and the localization from the CNN model.

The CNN model was implemented on an NVIDIA GeForce GTX 1060 6 GB GPU, 3.6 GHz Intel® Core™ i7 16 GB CPU Windows PC. The needle tip enhancement and augmentation methods were implemented in MATLAB 2018a. For the sub-problems in equations 9 and 10, the optimum values of $v=2$ and $\lambda=5$ were empirically determined. These values remained constant throughout the validation experiments. The needle tip detection framework was implemented in Keras 2.2.4 (on the Tensorflow 1.1.2 backend). In total, 5000 images from 20 video sequences were utilized for training the CNN model, while 1000 images from 10 other video sequences were used for validation. Additionally, 700 images from 20 video sequences that were not utilized in training or validation were utilized for testing the CNN model. The images were selected from continuous sequences having needle motion.

Figure 9:
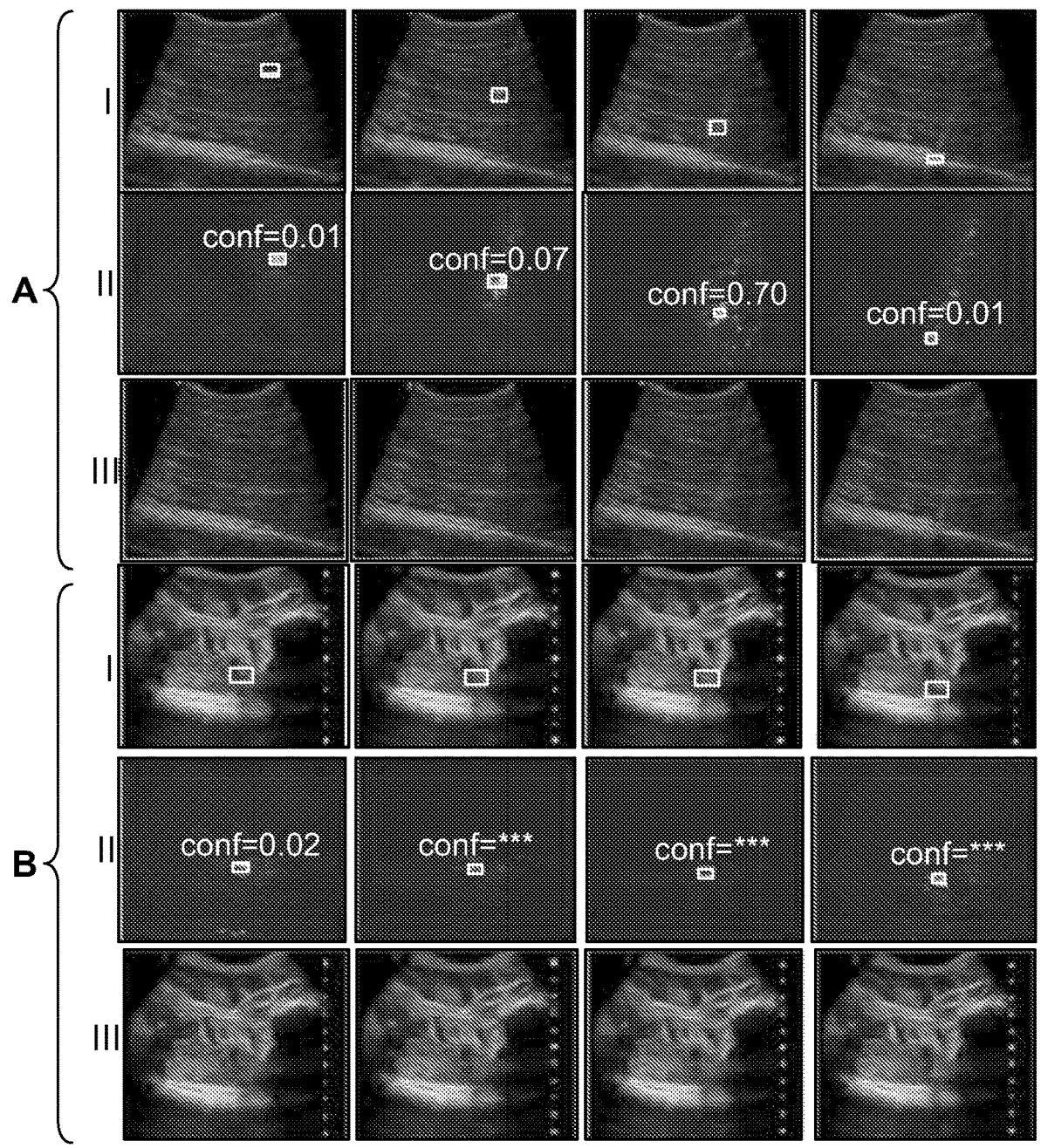
FIG. 9 shows needle tip localization results for consecutive frames from in-plane insertion of a 17 gauge needle and out-of-plane insertion of a 22 gauge needle.

FIG. 9 illustrates needle tip localization results for consecutive frames from in-plane insertion of a 17 gauge needle and out-of-plane insertion of a 22 gauge needle. Specifically, FIG. 9 illustrates needle tip detection and localization in four consecutive frames with (A) in-plane insertion of the 17 gauge Sonix GPS needle into chicken breast and (B) out-of-plane insertion of the 22 gauge needle into the porcine shoulder phantom. (I) illustrates the original image. The white box denotes the annotated ground-truth label. The ground-truth label can be determined with an EM tracking system for (A) and an expert sonographer for (B). (II) illustrates a detection result with a white bounding box overlaid on the enhanced image e(x, y). The inset value positioned alongside the white bounding box annotation denotes the detection confidence. (III) illustrates the localized needle tip wherein the center of the detected bounding box (e.g., the star) is overlaid on the original image.

It is noted that the needle tip is accurately localized despite the presence of other high-intensity interfering artifacts in the B-mode ultrasound data 202. If there is a point cloud arising from partial enhancement of the needle shaft, the CNN learns to automatically identify the needle tip at the distal end of the cloud in the enhanced image e(x, y). The temporal window for the needle tip visibility can be limited for out-of-plane insertion. However, the method of the present disclosure can be useful for tracking small movements of the needle tip close to the target. Additionally, the method of the present disclosure is agnostic to the needle type and the needle size utilized if the needle tip appears in the enhanced ultrasound image and needle motion is available in the B-mode ultrasound data 202. Increasing the training data size for each needle type can improve the performance of the systems and methods of the present disclosure.

CNN model comparisons provide for maximizing needle tip detection efficiency. For example, ablation studies alter the structural configuration of a deep learning framework to assess the impact on CNN model performance and are utilized to justify design choices. As such, the efficiency of the needle tip detection CNN framework was compared to that from alternative implementation approaches. The accuracy of needle tip detection can be determined using the mean average precision (mAP) metric on the validation dataset. The mAP metric is calculated as the average value of the precision across a set of 11 equally spaced recall levels, yielding one value that depicts the shape of the precision-recall curve. Table 3 shows the mAP metric for different configurations of the detection CNN. As shown in Table 3, the Detection CNN (with ELU)+p(x, y)+e(x, y) (in bold) of the present disclosure yields the highest mAP metric compared to alternative detection CNN frameworks.

TABLE 3

| Method | mAP |
| --- | --- |
| Detection CNN + p(x, y) | 0.202 |
| Detection CNN + e(x, y) | 0.867 |
| Detection CNN (with leakyReLU) + p(x, y) + e(x, y) | 0.914 |
| Detection CNN (with ELU) + p(x, y) + e(x, y) | 0.946 |

Evaluation of the detection CNN frameworks will now be discussed. First, the performance of the CNN with the raw ultrasound image p(x, y) as an input was examined. The detection efficiency of the CNN with the raw ultrasound image p(x, y) as an input is very low (20.2%) because, without the needle tip enhancement algorithm, the needle tip features are not clearly discernible and are overshadowed by other high intensity artifacts in the cluttered ultrasound image. The detection efficiency of the CNN with the enhanced image e(x, y) as the input yields a high mAP metric of 86.7% thereby demonstrating that the needle tip enhancement algorithm is efficient. Furthermore, the fusion of e(x, y) and p(x, y) yields the highest mAP metric of 94.6%.

The performance of the detection CNN model of the present disclosure was also compared against a similar model with Leaky Rectified Linear Unit (LeakyReLU) activation layers instead of an ELU wherein the fusion input 206 and other hyper parameters were maintained constant. As shown in Table 3, the detection CNN model with ELU of the present disclosure outperforms the detection CNN model with Leaky ReLU. It is noted that a batch size of 4 was utilized in the evaluation of the detection CNN frameworks because of the memory constraints of the GPU. It is expected that a larger batch size would have yielded an even higher mAP metric for the detection CNN model of the present disclosure.

Runtime performance of the CNN framework of the present disclosure will now be discussed. The CNN framework runs at 0.094±0.01 seconds per frame on the NVIDIA GeForce GTX 1060 GPU. Specifically, the CNN framework runs at 0.014 seconds per frame for enhancement, 0.06 seconds per frame for augmentation and 0.02 seconds per frame for detection. The runtime performance is approximately 10 frames per second (fps) and thereby achieves a fast needle tip localization framework. It is noted that the processing speed can be increased with additional computing resources. In frames where the needle tip is salient, the augmentation step is unnecessary, and the runtime speed increases to 29 fps.

The accuracy of the CNN framework can be increased by mitigating false needle tip detections. Since YOLO is a multi-object detection framework, YOLO can detect several bounding boxes with different confidence scores on a single input image. These false positives can be minimized by selecting the bounding box with the highest confidence score and utilizing a hard threshold of 0.35 for the confidence score. The hard threshold of 0.35 is an empirically determined value and is kept constant throughout validation. With this threshold, the CNN framework can yield an overall sensitivity of 98% and specificity of 91.8%. It is noted that the robustness of needle tip detection can be further improved by utilizing a bigger training dataset.

Figure 10:
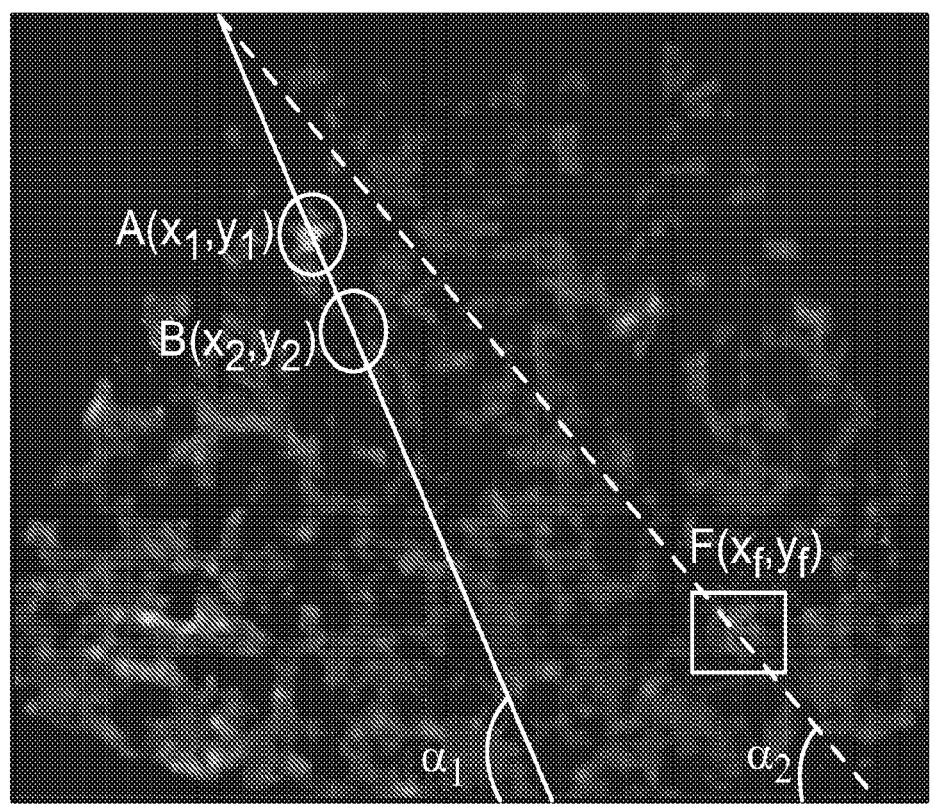
FIG. 10 illustrates elimination by the system of false positives from a trajectory estimation.

FIG. 10 illustrates elimination of needle tip localization false positives from a trajectory estimation. As shown in FIG. 10, points A and B lie along the correct trajectory whereas the bounding box with center F is a false positive. It is assumed that the needle tip detection framework accurately localized two previous spatial positions $A(x_1, y_1)$ and $B(x_2, y_2)$ in successive frames that are at least 30 pixels (approximately 5 mm) apart. From A and B, the needle trajectory $\alpha_1 = \tan^{-1}(|(y_2-y_1)/(x_2-x_1)|)$ is approximated. Then, for each subsequent detection with a bounding box at $F(x_1, y_1)$, the trajectory of angle $\alpha_2$ is estimated using points A and F with A as a static reference. If $|\alpha_1-\alpha_2|>10°$, the new detection is determined to be skewed from the correct trajectory and thus indicative of a false positive. Accordingly, the localization result is not utilized in calculating the localization error. During the localization process, false positives and true negatives lead to maintenance of the current needle tip position. As such, the elimination of need tip localization false positives from the trajectory estimation is robust to spatiotemporal redundancies.

Needle tip localization accuracy of the method of the present disclosure can be evaluated in view of the needle tip localization error and the performance of comparable methods. Overall, the needle tip localization error of the method of the present disclosure is 0.72±0.4 mm. A direct comparison with comparable methods is difficult because the method of the present disclosure does not require initial needle visibility. Therefore, the dataset collected for the method of the present disclosure is tailored for the evaluation of the method of the present disclosure.

Table 4 shows the results of a comparison between the method of the present disclosure and comparable methods. Specifically, Table 4 shows the results of the method of the present disclosure with detection CNN, a method disclosed in white paper "Convolution Neural Networks for Real-Time Needle Detection and Localization in 2D Ultrasound" by Cosmas Mwikirize et al. ("method of [16]"), and a method utilizing the Hough transform with the random sample consensus (RANSAC).

TABLE 4

| Method | Success (%) | Localization error (mm) | Overall processing time (s) |
| --- | --- | --- | --- |
| Proposed method (with detection CNN) | 100 | 0.72 ± 0.04 | 0.094 |
| Method of [16] | 44 | 1.04 ± 0.36 | 0.56 |
| Hough transform + RANSAC | 18 | 1.2 ± 0.32 | 0.74 |

Bold characters denote performance of the proposed method, which is the best when compared to alternative methods The embodiments of the present disclosure utilizing CNNs for detection and the method of [16] were compared by evaluating performance on the same set of 200 randomly selected ultrasound images with only in-plane needle insertion. It is noted that the method of the present disclosure with CNN detection outperforms the method of [16] in both needle tip localization accuracy and computational efficiency. Localization errors of approximately 2 mm (i.e., 56% of the data) were discarded for the purpose of the comparison. A one-tailed paired test shows that the difference between the localization errors from the method of the present disclosure and the method of [16] is statistically significant (p<0.005). The localization accuracy obtained from the method of [16] is worse than previously reported because a more challenging dynamic dataset with very low shaft intensity was utilized for validation.

The systems/methods of the present disclosure utilizing CNN for detection, and the systems/methods utilizing the Hough transform and the RANSAC, were also compared. Specifically, the systems/methods of the present disclosure utilizing CNN detection were compared with an intensity-based method that directly localizes the needle tip utilizing the Hough transform and the RANSAC. As shown in Table 4, the method utilizing the Hough transform and the RANSAC achieved success in only 18% of the dataset (neglecting errors >2 mm), with an overall localization error of 1.2±0.32 mm.

Table 5 shows the determined needle localization from the maximum intensity in e(x, y), (i.e., the method of the present disclosure without the tip detection step).

TABLE 5

| Localization approach | Ground truth | # of images | Error (mm) |
|---|---|---|---|
| Proposed method (with detection CNN) | Tracking system | 250 | 0.76 ± 0.03 |
| Proposed method (with detection CNN) | Expert | 450 | 0.69 ± 0.05 |
| Proposed method (with detection CNN) (overall) | | 700 | 0.72 ± 0.04 |
| Highest intensity in e(x, y) (without detection CNN) | Tracking system | 250 | 0.94 ± 0.04 |
| Highest intensity in e(x, y) (without detection CNN) | Expert | 450 | 1.12 ± 0.05 |
| Highest intensity in e(x, y) (without detection CNN) (overall) | | 700 | 1.06 ± 0.04 |

Bold characters denote performance of the proposed method, which is the best when compared to alternative methods The results shown in Table 5 demonstrate that the localization accuracy is worse without the detection CNN framework. As such, without the benefit of implicitly learning heuristic features associated with the needle tip via deep learning, there is a higher likelihood of localizing artifacts with similar intensity to the needle tip.

Figure 11:
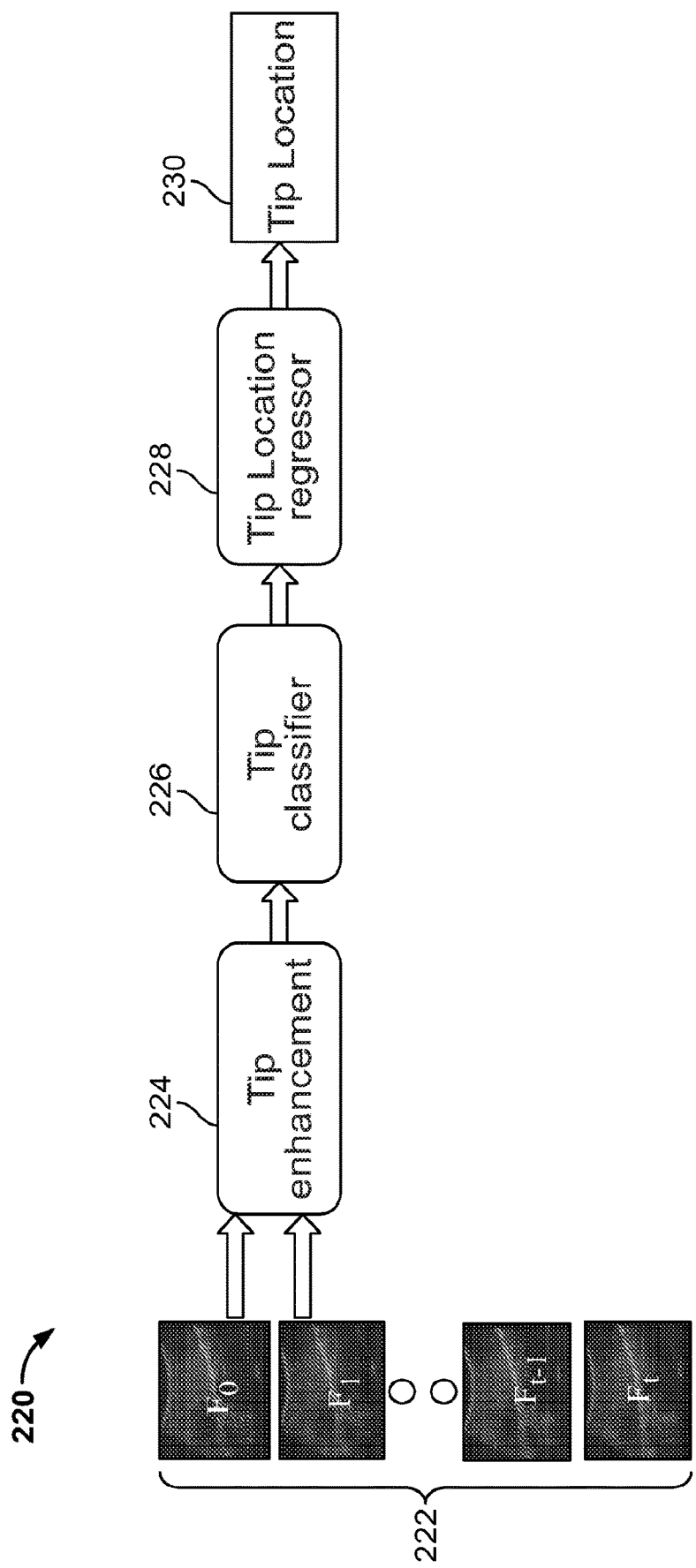
FIG. 11 is a block diagram illustrating another embodiment of the system and method of the present disclosure, wherein a convolutional neural network localizes a needle tip in ultrasound images.

FIG. 11 is a block diagram 220 illustrating another embodiment of the system and method of the present disclosure, wherein a convolutional neural network localizes a needle tip in temporal ultrasound data. The framework accommodates variations between images captured under different imaging scenarios and needle insertion profiles. The method of the present disclosure targets both out-of-plane and in-plane inserted needles in which the needle tip exhibits low contrast compared to the rest of the ultrasound image.

As shown in FIG. 11, the systems and methods of the present disclosure consists of four processes based on input ultrasound frames $F_0$ to $F_t$ 222. Specifically, the processes include needle tip enhancement 224, needle tip classification 226, needle tip location regression 228 and needle tip location 230. The needle tip enhancement process 224 comprises enhancement of the needle tip from two consecutive ultrasound frames. The needle tip classification process 226 determines, using a classifier network, whether the enhanced image contains substantial needle tip information. The needle tip classification process 226 is necessary because the hand-inserted needle tip does not move smoothly through space and as such frames will exist in the sequence where the needle tip has not changed spatial location. The needle tip location regression process 228 estimates the needle tip location using a keypoint regression CNN. These processes will be described in detail below.

The two-dimensional B-mode ultrasound images utilized in the learning experiments were collected using two imaging systems including the SonixGPS (Analogic Corporation, Peabody, Mass., USA) with a handheld C5-2/60 curvilinear probe and the Clarius C3 two-dimensional handheld wireless ultrasound (Clarius C3, Clarius Mobile Health Corporation, Burnaby, BC, Canada). In addition, experiments were performed on freshly excised bovine tissue, porcine tissue and chicken breast overlaid on a lumbosacral spine phantom, with insertion of a 17 gauge SonixGPS vascular access needle (Analogic Corporation, Peabody, Mass., USA) and a 22 gauge spinal Quincke-type needle (Becton, Dickinson and Company, Franklin Lakes, N.J., USA).

The needles were inserted both in-plane (30° to 70° insertion angle) and out-of-plane up to a depth of 70 mm. For the SonixGPS needle, tip localization data was collected from an EM tracking system (Ascension Technology Corporation, Shelburne, Vt., USA). During the experiments, minor motion events were simulated by exerting pressure on the tissue with the probe and probe rotation. In total, 60 volumes were collected (30 in-plane, 30 out-of-plane: 40 with Sonix GPS system and 20 with Clarius C3 system), with each video sequence having more than 600 frames. In training and validating the needle tip classifier, 7000 positive examples (enhanced images with the tip) and 5000 negative examples (enhanced images without tip information) were utilized. Regarding needle tip location regression, 7000 images (only positive examples) for training and validation were utilized and 500 images from 20 sequences not used for training and validation were utilized for testing.

In the needle tip enhancement process 224, the logical difference of consecutive frames z(x, y) is computed from the ultrasound frame sequence $F_0, F_1 \ldots F_{t-1}, F_t$ 222 where the subscript denotes the respective temporal position and $F_0$ is the first frame. For a current frame n(x, y) and a previous frame m(x, y), z(x, y) can be calculated by equation 11 below:

$$z(x,y) = m^c(x,y) \wedge n(z,y) \qquad \text{Equation 11}$$

Figure 12:
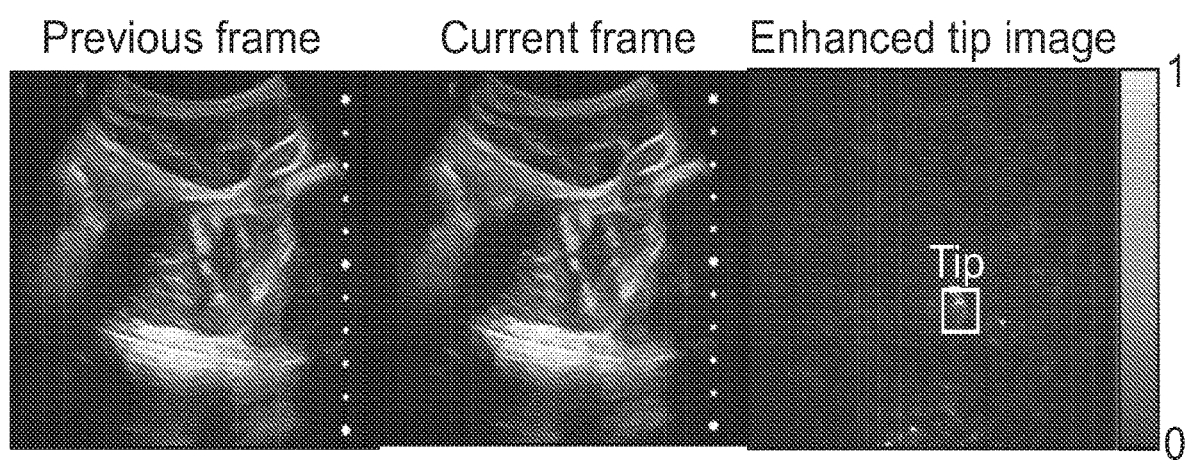
FIG. 12 illustrates needle tip enhancement results according to step 244 of FIG. 11.

In equation 11, $m^c(x, y)$ is the bitwise complement of m(x, y), while $\wedge$ is the bitwise AND logical operation. This logical differencing routine produces intensities T: [0, 255] representative of the difference between the two frames. Therefore, subtle motion between the two frames will be captured. It is noted that the needle tip will provide the most prominent feature in z(x, y). To compensate for irrelevant motion events, a 12×12 median filter is applied to z(x, y) and further tip augmentation is not performed. FIG. 12 shows the result of the tip enhancement process 224.

Figure 13:
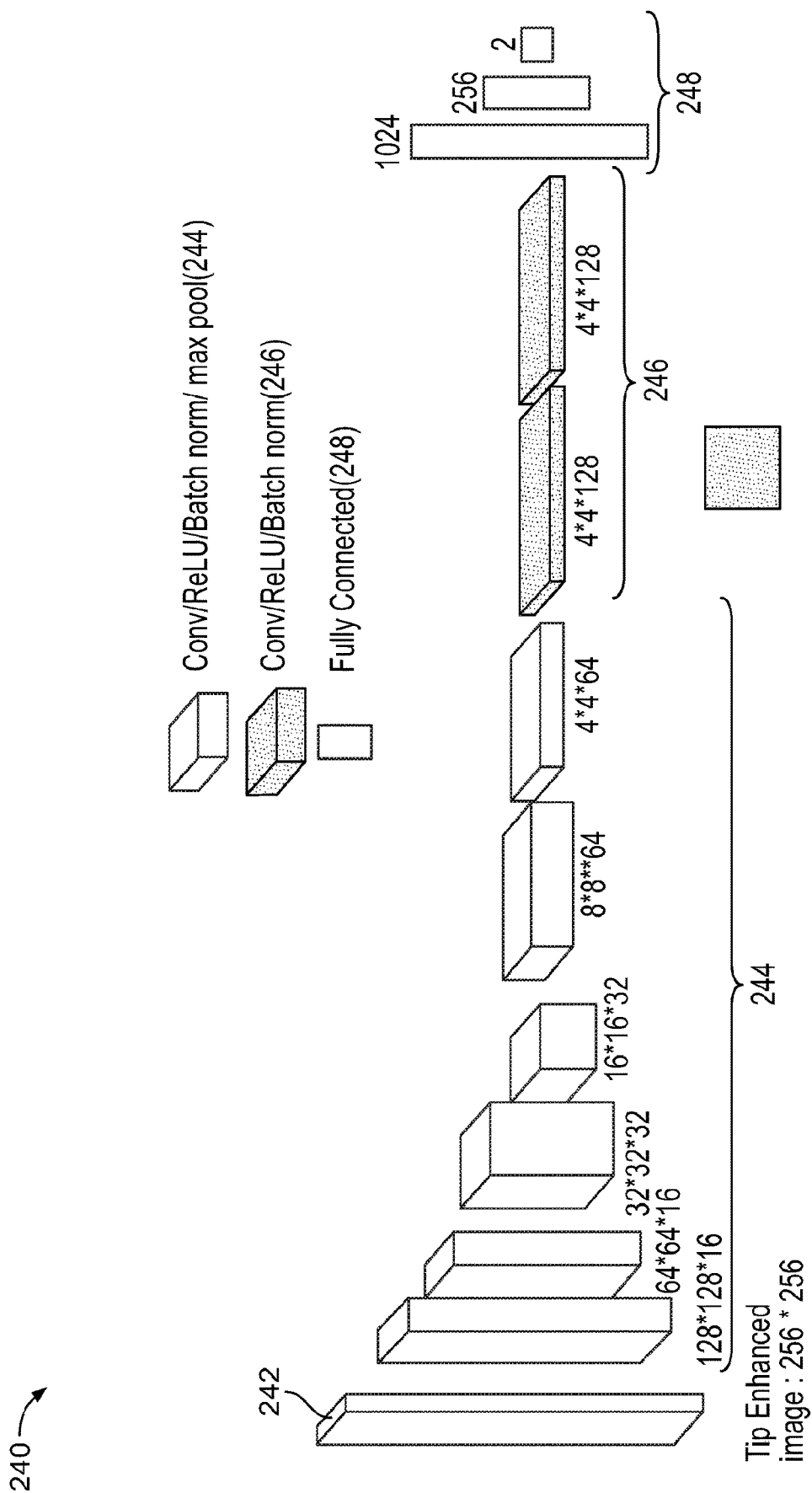
FIG. 13 is a block diagram illustrating a convolutional neural network capable of performing needle tip classification according to process 226 of FIG. 11.

FIG. 13 is a block diagram illustrating a convolutional neural network 240 capable of performing processing steps for tip classification process 226 of FIG. 11. The network consists of a needle tip enhanced image 242, 6 blocks of convolution, Rectified Linear Unit (ReLU) activation layers, batch normalization and max pooling layers 244, 2 blocks of convolution, ReLU and batch normalization layers 246, and 3 fully connected layers 248. The input needle tip enhanced image 242 consists is a 256×256 image. All convolution layers utilize a 3×3 kernel, and a stride/padding of 1 pixel. The max pooling layers utilize a 2×2 kernel.

Positive and negative examples for the enhanced needle tip (see FIG. 14) can be labeled by a radiologist experienced in interventional radiology while referring to the corresponding original ultrasound sequences and EM tracking information for tracked needles. In positive examples, the needle tip exists as a distinct high intensity feature, a few pixels thick, against a low intensity background. This type of feature is lacking from negative training examples. If other high intensity noisy artifacts exist, the classifier can differentiate them from the needle. It is noted that the last feature map for the classification task, from the last fully connected (FC) layer, is a vector of dimension 1×1×2, (i.e., it is meant to differentiate images of two classes: those with an enhanced needle tip and those without it). A Softmax activation is applied to this feature map and the Log Loss is utilized to calculate deviations between the network output and the ground-truth. During training, a stochastic gradient descent with momentum (SGDM) optimizer, and initial learning rate of $10^{-2}$ is utilized.

The architecture of the tip regression CNN mirrors the classification CNN of FIG. 13, with the exception of terminating in a 4-output FC layer (the needle tip location is defined by two keypoints). In essence, there is a cascade of two twin CNNs which share all of the learned layers but differ only in the output. During training and testing, the needle tip classification process 226 and the needle tip location regression process 228 are run in series.

Figure 14:
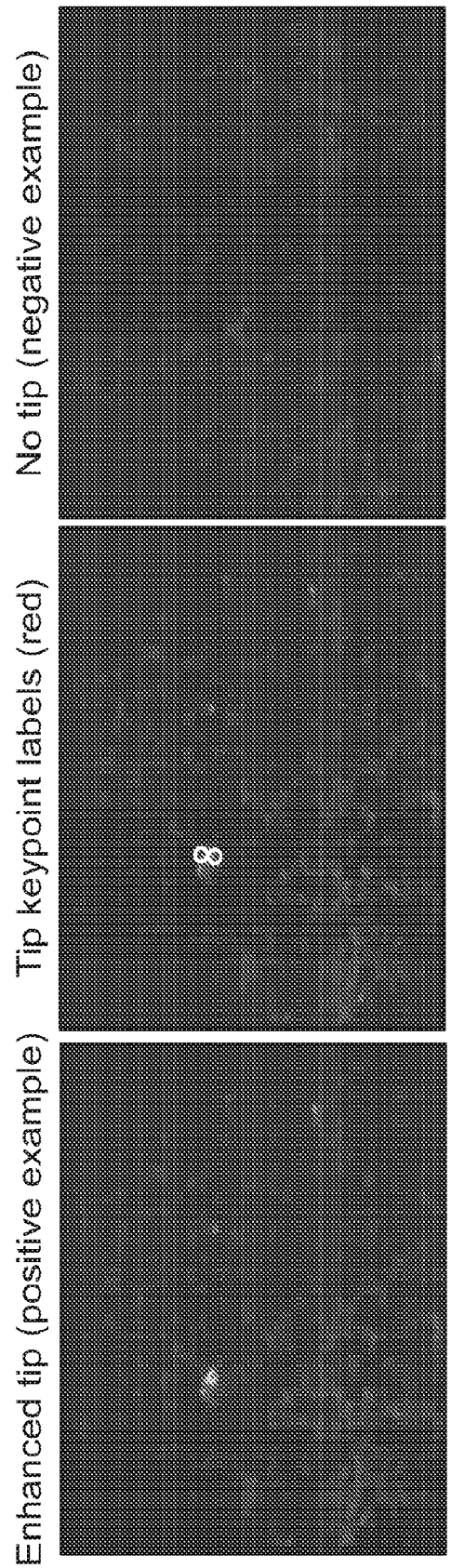
FIG. 14 shows needle tip labels for a needle tip classification neural network and a needle tip regression convolutional neural network.

The input to the regression CNN is the needle tip enhanced image 242 and the corresponding location labels. Keypoints for the needle tip are labeled as shown in FIG. 14. Two keypoints on the needle tip are utilized (e.g., $t_p$: $(x_1, y_1)$, $(x_2, y_2)$). The utilization of the two keypoints constrains the spatial likelihood of the needle tip since the enhanced tip feature is not geometrically definable for labeling purposes. The keypoint labels are placed geometrically opposite along a line through the center of the enhanced needle tip feature and the pixel at the distal end.

The enhanced images are augmented by rotating them through 90°, 180° and 270°. The labels are computationally manipulated to match the rotated images. From the original 7000 enhanced images, this yields 28,000 training examples. Further, the labels are normalized to be in the range Q: [−1, 1]. Since the initial labels are in the range [1,256], scaling reduces the magnitude of the Mean Squared Error (MSE), which is utilized as the loss function metric, and the magnitude of the gradients. This quickens the training process and ensures stable convergence. At test time, the outputs are rescaled to match the original data.

The last feature map for the needle tip location regression process 228, from the last FC layer, is a vector of dimension 1×1×4, containing the four coordinates of the two labels: $(x_1, y_1)$, $(x_2, y_2)$. During training, the parameters include the RMSprop optimizer, an initial learning rate of $10^{-3}$, and a mini batch size of 32. At test time, the top location $T(x_t, y_t)$ is directly obtained from the CNN outputs as the average of the x and y outputs, i.e., $x_t=(x_1+x_2)/2$, $y_t=(y_1+y_2)/2$. Since a region proposal step or anchor boxes are unnecessary to tell the network where to look, the framework provides a single-shot approach for needle tip localization.

Figure 15:
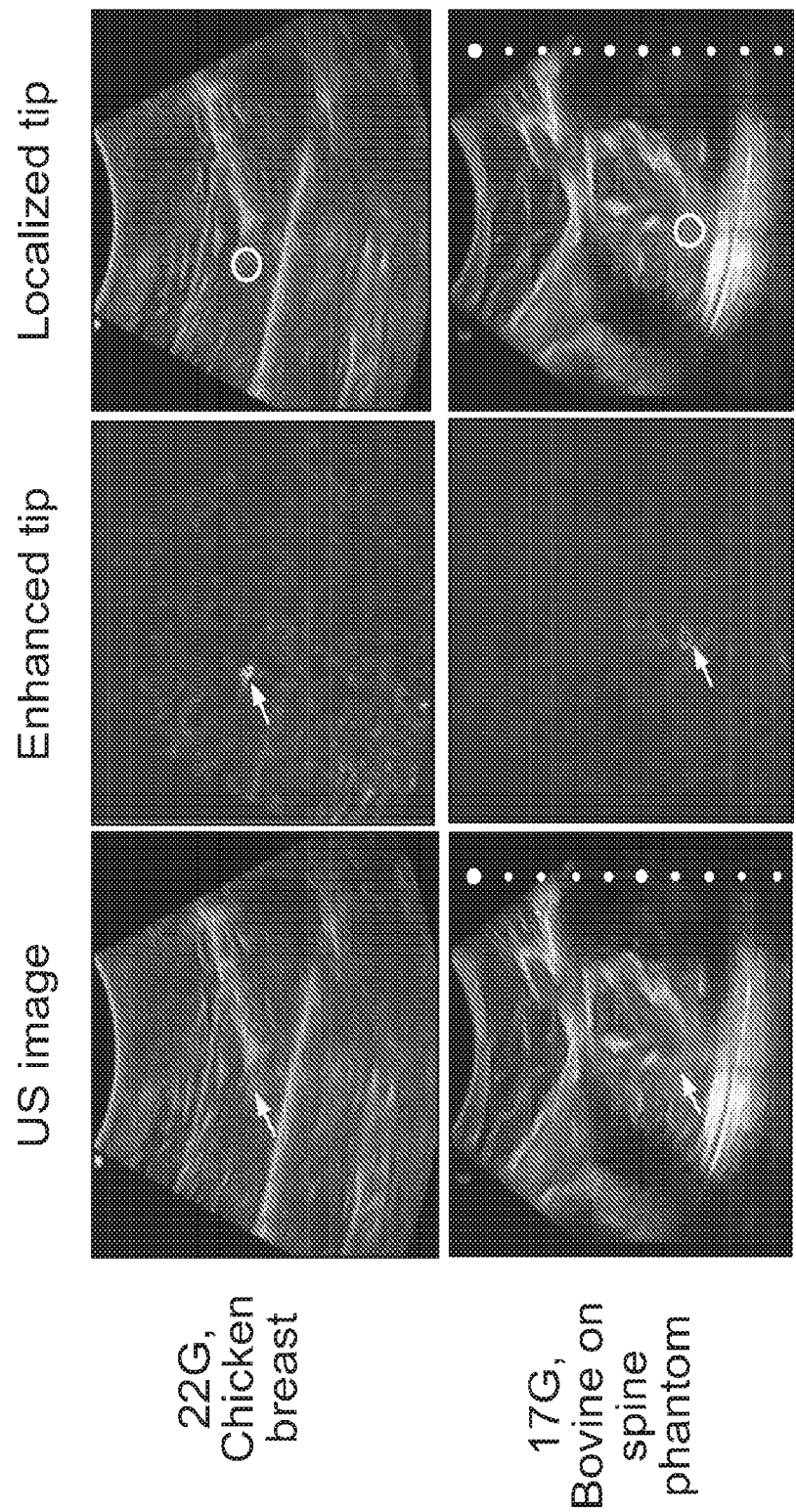
FIG. 15 shows needle tip localization results for insertion of a 17 gauge needle and insertion of a 22 gauge needle.

The qualitative results of the method of the present disclosure will now be discussed. FIG. 15 shows examples of needle tip enhancement and localization. It is noted that the CNN framework accurately localizes the needle tip despite that the needle tip has low contrast and the needle shaft information is not visible. This is because the method of the present disclosure detects subtle intensity changes arising from needle tip motion, that are otherwise not easily discernible with the naked eye. Further, localization accuracy is generally resilient to high intensity artifacts in the rest image.

The classification accuracy of the method of the present disclosure will now be discussed. The classification CNN achieves an overall sensitivity and specificity of 88% and 82% respectively on test sequences. By comparison, the method disclosed in white paper "Learning Needle Tip Localization from Digital Subtraction in 2D Ultrasound" by Cosmas Mwikirize et al. ("Digital Subtraction Method") achieved sensitivity and specificity of 95% and 90% respectively. Specifically, the Digital Subtraction Method outperforms the method of the present disclosure in the presence of increased motion artifacts in the imaging medium due to an included computationally expensive step for noise removal. However, in relatively stable sequences, the classification accuracy between the method of the present disclosure and the Digital Subtraction Method was similar (98% vs 97%). Therefore, the method of the present disclosure is suitable for procedures where there is minimal motion from physiological events (e.g., lumbar facet injections and peripheral nerve blocks). It is noted that a larger training dataset would improve the classification accuracy of the method of the present disclosure even in the presence of motion artifacts.

The needle tip localization error of the method of the present disclosure will now be discussed. The ground-truth needle tip location is determined from the original ultrasound sequences by a radiologist, with augmentation from the EM tracking system. Needle tip localization error is determined from the Euclidean Distance between the automatically determined needle tip location from the method of the present disclosure and the ground truth. Based on an evaluation for both in-plane (IP) and out-of-plane (OP) needle insertions, the method of the present disclosure provides for an overall needle tip localization error of 0.55±0.07 mm Table 6 shows a comparative analysis between the method of the present disclosure (i.e., proposed method) and other needle tip localization methods.

TABLE 6

| Method | Test data | error (mm) | Processing time (s) | Success rate |
|---|---|---|---|---|
| Proposed method | 500(250 IP, 250 OP) | 0.55 ± 0.07 | 0.015 (67 fps) | 94% |
| Method in [1] | 500(250 IP, 250 OP) | 0.78 ± 0.08 | 0.091 (11 fps) | 97% |
| Method in [2] | 250 (IP) | 1.23 ± 0.45 | 0.42 (2 fps) | 52% |

As shown in Table 6, the proposed method outperforms the other methods with a statistically significant improvement (p<0.005). Since the method in [2] requires needle shaft information, 250 test images were utilized from the sequences with in-plane needle insertion for its evaluation. For all methods, an error cap of 2 mm was imposed as a measure of needle tip localization success. By dropping the worst 3% cases of the data analyzed with the method in [1] in order to obtain a 94% success rate similar to the proposed method, the localization error dropped to 0.73±0.07 mm which demonstrates that the proposed method provides improved results (p<0.005). Most of the failed cases (6%) resulted from the top localization network regressing onto a false artifact in the enhanced image. It is noted that performance in this regard can be improved with a larger training dataset.

The systems and methods of the present disclosure provide for an improvement in overall processing time. The experiments were executed on an NVIDIA GeForce GTX 1060 6 GB GPU, 3.6 GHz Intel® Core™ i7 16 GB CPU Windows PC and the method of the present disclosure was implemented in MATLAB 2018a using the Deep Learning Toolbox. The learning framework is trained offline and tested with offline video sequences of ultrasound data. Average processing time for the enhancement process is 0.002 seconds per image. Classification of the enhanced image can be an average of 0.007 seconds while needle tip localization requires 0.006 seconds. As such, the overall processing time is 0.015 seconds (67 fps) which provides a 509% improvement, in fps, over the method in [1].

Different CNN structures consisting of different numbers of convolution and pooling layers were investigated for the regression component of the learning framework. In addition, relative performance using the normalized Root Mean Square Error (RMSE) on the validation dataset was evaluated. The method of the present disclosure provides for a normalized RMSE of 0.006 which is better than that achieved by the maximum network depth for the 256×256 image input consisting of 8 convolution layers with pooling after each layer (0.014) and a network with only 6 convolutions (0.05). In addition, the performance of different optimizers in the regression network was compared. The following optimizers achieved the correspondingly indicated normalized RMSE: RMSprop (0.006), Adam (0.05), and SGDM (0.14). It is noted that there was no significant improvement in performance when using dropout layers in the regression network.

Having thus described the system and method in detail, it is to be understood that the foregoing description is not intended to limit the spirit or scope thereof. It will be understood that the embodiments of the present disclosure described herein are merely exemplary and that a person skilled in the art can make any variations and modification without departing from the spirit and scope of the disclosure. All such variations and modifications, including those discussed above, are intended to be included within the scope of the disclosure.

What is claimed is:

1. A method for real-time localization of a medical device in a video, comprising the steps of:
    receiving at a processor a plurality of frames from the video;
    identifying by the processor one of the plurality of frames as a background image and a frame adjacent to the background image as a current image;
    performing by the processor a bitwise complement operation on the background image to generate a complement image; and
    performing by the processor a pointwise logical AND operation on the complement image and the current image to identify the location of the medical device.

2. The method of claim 1, further comprising the step of enhancing the medical device using a Split Bregman process.

3. The method of claim 1, wherein the medical device is a needle.

4. The method of claim 3, wherein a tip of the needle is inserted in-plane.

5. The method of claim 3, wherein a tip of the needle is inserted out-of-plane.

6. The method of claim 3, wherein the needle's insertion angle is not known.

7. The method of claim 3, wherein the needle is non-linear.

8. The method of claim 1, further comprising the step of setting a threshold correlation coefficient for skipping a frame due to insignificant motion.

9. The method of claim 1, wherein the video is an ultrasound video.

10. The method of claim 1, further comprising the step of enhancing image data representing the medical device using a convolution neural network.

11. A system for real-time localization of a medical device in a video, comprising:
    a processor; and
    a memory in communication with the processor, the memory having computer instructions stored thereon which, when executed, cause the processor to perform the following steps:
    receiving a plurality of frames from the video;
    identifying one of the plurality of frames as a background image and a frame adjacent to the background image as a current image;
    performing a bitwise complement operation on the background image to generate a complement image; and
    performing a pointwise logical AND operation on the complement image and the current image to identify the location of the medical device.

12. The system of claim 11, wherein the instructions further cause the processor to enhance the medical device using a Split Bregman process.

13. The system of claim 11, wherein the medical device is a needle.

14. The system of claim 13, wherein a tip of the needle is inserted in-plane.

15. The system of claim 13, wherein a tip of the needle is inserted out-of-plane.

16. The system of claim 13, wherein the needle's insertion angle is not known.

17. The system of claim 13, wherein the needle is non-linear.

18. The system of claim 11, wherein a threshold correlation coefficient is set for skipping a frame due to insignificant motion.

19. The system of claim 11, wherein the video is an ultrasound video.

20. The system of claim 11, wherein the instructions further cause the processor to enhance image data representing the medical device using a convolution neural network.

21. A non-transitory computer-readable medium having computer-readable instructions stored thereon which, when executed by a computer system, cause the computer system to perform the steps of:
    receiving at a processor a plurality of frames from a video;
    identifying by the processor one of the plurality of frames as a background image and a frame adjacent to the background image as a current image;
    performing by the processor a bitwise complement operation on the background image to generate a complement image; and
    performing by the processor a pointwise logical AND operation on the complement image and the current image to identify the location of a medical device.

22. The non-transitory computer readable medium of claim 21, further comprising the step of enhancing the medical device using a Split Bregman process.

23. The non-transitory computer readable medium of claim 21, wherein the medical device is a needle.

24. The non-transitory computer readable medium of claim 23, wherein a tip of the needle is inserted in-plane.

25. The non-transitory computer readable medium of claim 23, wherein a tip of the needle is inserted out-of-plane.

26. The non-transitory computer readable medium of claim 23, wherein the needle's insertion angle is not known.

27. The non-transitory computer readable medium of claim 23, wherein the needle is non-linear.

28. The non-transitory computer readable medium of claim 21, further comprising the step of setting a threshold a correlation coefficient for skipping a frame due to insignificant motion.

29. The non-transitory computer readable medium of claim 21, further comprising the step of enhancing image data representing the medical device using a convolution neural network.

* * * * *

UNITED STATES PATENT AND TRADEMARK OFFICE
CERTIFICATE OF CORRECTION

PATENT NO. : 11,426,142 B2  
APPLICATION NO. : 17/268321  
DATED : August 30, 2022  
INVENTOR(S) : Cosmas Mwikirize, John L. Nosher and Ilker Hacihaliloglu Page 1 of 1

It is certified that error appears in the above-identified patent and that said Letters Patent is hereby corrected as shown below:

On the Title Page

On page 4, item (56) under the References Cited Other Publications Column, the second column, the tenth reference down, the name "Zveringham, et al." should be deleted and replaced with the name "Everingham, et al."

Signed and Sealed this  
Seventh Day of March, 2023

Katherine Kelly Vidal  
*Director of the United States Patent and Trademark Office*